United States Patent
Miyazaki et al.

(10) Patent No.: US 12,060,616 B2
(45) Date of Patent: Aug. 13, 2024

(54) METHOD FOR ASSISTING DETERMINATION OF HEMATOLOGICAL STAGE OF CHILDHOOD ACUTE LYMPHOBLASTIC LEUKEMIA

(71) Applicant: OTSUKA PHARMACEUTICAL CO., LTD., Tokyo (JP)

(72) Inventors: Yoshihide Miyazaki, Osaka (JP); Yukari Umehara, Osaka (JP); Osamu Kosaka, Osaka (JP); Kimiyoshi Sudou, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 217 days.

(21) Appl. No.: 16/319,024

(22) PCT Filed: Jul. 18, 2017

(86) PCT No.: PCT/JP2017/025913
§ 371 (c)(1),
(2) Date: Jan. 18, 2019

(87) PCT Pub. No.: WO2018/016474
PCT Pub. Date: Jan. 25, 2018

(65) Prior Publication Data
US 2019/0161810 A1    May 30, 2019

(30) Foreign Application Priority Data
Jul. 19, 2016   (JP) .................................. 2016-141793

(51) Int. Cl.
*C12Q 1/6886* (2018.01)
*C12Q 1/68* (2018.01)
(Continued)

(52) U.S. Cl.
CPC ............. *C12Q 1/6886* (2013.01); *C12Q 1/68* (2013.01); *C12Q 1/686* (2013.01); *G16H 50/20* (2018.01);
(Continued)

(58) Field of Classification Search
CPC ......................... C12Q 1/6886; C12Q 2600/158
See application file for complete search history.

(56) References Cited

U.S. PATENT DOCUMENTS

| | | | |
|---|---|---|---|
| 2010/0041055 A1 | 2/2010 | Davies et al. | |
| 2011/0067123 A1* | 3/2011 | Andersen .................. | C12Q 1/34 514/354 |

(Continued)

FOREIGN PATENT DOCUMENTS

WO      2014/115779 A1      7/2014

OTHER PUBLICATIONS

Koga, D. et al, Google Patents translation of WO2014115779A1 (original document cited in IDS), 13 pages (Jul. 31, 2014). (Year: 2014).*

(Continued)

*Primary Examiner* — Diana B Johannsen
(74) *Attorney, Agent, or Firm* — Sughrue Mion, PLLC

(57) ABSTRACT

Provided are a method for assisting in determining the hematological stage of childhood acute lymphoblastic leukemia (child ALL), and an in-vitro diagnostic pharmaceutical product usable in the method. The method for assisting in determining the hematological stage of child ALL comprises the steps of (1) obtaining the mRNA level of Wilms' tumor-1 gene (WT1) in at least one of the biological samples of peripheral blood and bone marrow fluid from a test subject; (2) obtaining the GAPDH mRNA level in the biological sample; and (3) calculating an index value necessary for assisting in the determination based on the ratio of (Continued)

the WT1 mRNA level obtained in step (1) to the GAPDH mRNA level obtained in step (2).

15 Claims, 8 Drawing Sheets

Specification includes a Sequence Listing.

(51) Int. Cl.
    *C12Q 1/686* (2018.01)
    *G16H 50/20* (2018.01)
    *C12N 15/09* (2006.01)

(52) U.S. Cl.
    CPC ........ *C12N 15/09* (2013.01); *C12Q 2600/106* (2013.01); *C12Q 2600/112* (2013.01); *C12Q 2600/118* (2013.01); *C12Q 2600/156* (2013.01); *C12Q 2600/158* (2013.01); *C12Y 102/01009* (2013.01)

(56) References Cited

U.S. PATENT DOCUMENTS

2015/0031574 A1* 1/2015 Murakami ............. C12Q 1/706
    506/9
2016/0333415 A1 11/2016 Saijo et al.

OTHER PUBLICATIONS

Hu Wen-ting, et al. "Detection of WT1 gene by real-time quantative PCR in childhood leukemia", J Clin Pediatr, 2008, vol. 26, pp. 655 to 659 (5 pages total).
Yuichi Sakamoto et al.;"Toin ni Okeru WTImRNA Teiryo Kensa Shiko Shorei no Kento", The Japanese Journal of Clinical Pathology, vol. 56, 2008, p. 278.
Haruo Sugiyama, "WT1 mRNA Kakusan Zofuku Kensa", Modern Media, 2012, vol. 58, pp. 178-181.
Ujj, Zsofia et al., "WT1 Overexpression Affecting Clinical Outcome in Non-Hodgkin Lymphomas and Adult Acute Lymphoblastic Leukemia", Pathol. Oncol. Res, vol. 20, 2014, pp. 565-570.
Ujj, Zsofia et al., "WT1 Expression in Adult Acute Myeloid Leukemia: Assessing its Presence, Magnitude and Temporal Changes as Prognostic Factors", Pathol. Oncol. Res., vol. 22, 2016, pp. 217-221.
"WT1 mRNA Assay Kit II "Otsuka"", Otsuka Pharmaceutical Co, 3rd ed. Jul. 2015, pp. 1-8 (18 pages total).
"Prognostic value of quantitative analysis of WT1 gene transcripts in adult acute lymphoblastic leukemia", Haematologica/The Hematology Journal, 2006, vol. 91, No. 2, p. 270-271.
L Boublikova et al., "Wilms' tumor gene 1 (WT1) expression in childhood acute lymphoblastic leukemia: a wide range of WT1 expression levels, its impact on prognosis and minimal residual disease monitoring", Leukemia, vol. 20, 2006, pp. 254-263.
Mahdi Shabani et al., "Expression profile of orphan receptor tyrosine kinase (ROR1) and Wilms' tumor gene 1 (WT1) in different subsets of B-cell acute lymphoblastic leukemia", Leukemia & Lymphoma, vol. 49, No. 7, Jul. 2008, pp. 1360-1367.
Jiann-Shiuh Chen et al., "Comparison of minimal residual disease (MRD) estimated by flow cytometry and by real-time quantitative PCR of Wilms tumor gene 1 (WT1) transcript expression in children with acute lymphoblasitc leukemia", Leukemia Research, vol. 31, 2007, pp. 1351-1357.
Antonia Busse et al., "Wilms' tumor gene 1 (WT1) expression in subtypes of acute lymphoblastic leukemia (ALL) of adults and impact on clinical outcome", Ann Hematol, vol. 88, 2009, pp. 1199-1205.
Shao-Yan Hu et al., "The significance of detecting WT1 expression in childhood acute leukemias", Pediatric Hematology and Oncology, vol. 27, 2010, pp. 581-591.
Bing Xu et al., "Simultaneous detection of MDR1 and $WT_1$ gene expression to predict the prognosis of adult acute lymphoblastic leukemia", Hematology, vol. 15, No. 2, 2010, pp. 74-80.
M.J. Borowitz et al., "B lymphoblastic leukemia/ lymphoma, not otherwise specified", Fourth Edition, Lyon, IARC Press, 2008, pp. 168-178.
Tomohei Nakao, "Non-malignant elevation of Wilms tumor gene (WT1) expression is frequently observed in the blood and bone marrow of childhood acute leukemia in remission and in benign blood diseases", Doctoral (medicine) Dissertation, The University of Tsukuba (Kou No. 5112), 2009, pp. 638-640.
R. Zhang et al., "Comparison of minimal residual disease (MRD) monitoring by WT1 quantification between childhood acute myeloid leukemia and acute lymphoblastic leukemia", European Review for Medical and Pharmacological Sciences, vol. 19, 2015, pp. 2679-2688.
Ching-Hon Pui, M.D. et al., "Acute Lymphoblastic Leukemia", The New England Journal of Medicine, vol. 350, 2004, p. 1535-1548.
"Prognosis and Prognosis Prediction Factors", The Japanese Journal of Clinical Hematology, vol. 50, 2009, p. 230-243.
Gary Gilliland et al., "Analysis of cytokine mRNA and DNA: Detection and quantitation by competitive polymerase chain reaction", Proc. Natl. Acad. Sci, vol. 87, Apr. 1990, pp. 2725-2729.
Brigitte Debuire et al., "Nonisotopic Competitive RT-PCR Assay to Measure MDR1 Gene Expression", Clinical Chemistry, vol. 41, No. 6, 1995, p. 819-825.
Nicholas C.P. Cross et al. "Competitive Polymerase Chain Reaction to Estimate the Number of BCR-ABL Transcripts in Chronic Myeloid Leukemia Patients After Bone Marrow Transplantation", Blood, vol. 82, No. 6, 1993, pp. 1929-1936 (9 pages).
Kunio Kitamura et al., "Clinical usefulness of WT1 mRNA expression in bone marrow detected by a new WT1 mRNA assay kit for monitoring acute myeloid leukemia: a comparison with expression of WT1 mRNA in peripheral blood", Int J Hematol, vol. 103, 2016, p. 53-62.
"WT1 mRNA Assay Kit II "Otsuka"", Otsuka Pharmaceutical Co 6th edition, Mar. 2013, pp. 1-8 (20 pages).
International Preliminary Report on Patentability with translation of Written opinion dated Jan. 22, 2019, in counterpart international application No. PCT/JP2017/025913.
International Search Report dated Aug. 15, 2017, in counterpart International Application No. PCT/JP2017/025913.
Shao-Yan Hu et al., "The Significance of Detecting WT1 Expression in Childhood Acute Leukemias", Pediatric Hematology and Oncology, vol. 27, Issue 8, pp. 581-591 (2010) (abstract; 4 pages total).
Office Action dated Jan. 13, 2021 from the European Patent Office in EP Application No. 17 830 990.2.
Extended European Search Report dated Dec. 16, 2019, from the European Patent Office in European Application No. 17830990.2.
Hiroyasu Ogawa et al., "WT1 Gene Transcript Assay for Relapse in Acute Leukemia after Transplantation", Leukemia and Lymphoma, Sep. 1, 2004, vol. 45, No. 9, pp. 1747-1753 (7 pages total).
Engy El Khateeb et al., "Preferentially Expressed Antigen of Melanoma (PRAME) and Wilms' Tumor 1 (WT 1) Genes Expression in Childhood Acute Lymphoblastic Leukemia, Prognostic Role and Correlation with Survival", Open Access Macedonian Journal of Medical Sciences, Mar. 15, 2015, vol. 3, No. 1, pp. 57-62 (6 pages total).
Adel A Hagag et al., "Prognostic Impact of WT-1 Gene Expression in Egyptian Children with Acute Lymphoblastic Leukemia, Mediterranean Journal of Hematology and Infectious Diseases", Jan. 1, 2016, vol. 8, pp. 1-8 (8 pages total).
Office Action, dated Mar. 3, 2022, issued by the State Intellectual Property Office of People's Republic of China in Chinese Patent Application No. 201780044530.8.
Wang, Xu-li et al., "Expression of WT1 Gene in Acute Leukemia in Children and Its Clinical Significance", J. Appl. Clin. Pediatr., 2010, vol. 25, No. 3, pp. 167-169 (3 pages total).
Li, Rong et al., "Detection Wilm's Tumor Gene Expression in Peripheral Blood and Its Clinical Significance of Acute Lymphocytic Leukemia Children", J. Appl. Clin. Pediatr., 2005, vol. 20, No. 1. pp. 27-28 (2 pages total).

(56) References Cited

OTHER PUBLICATIONS

Shi, Hong-song et al., "Expressions of WT1 and eIF4E genes in children with acute lymphocytic leukemia and the clinical significances", J. Chin. Pract. Diagn. Ther., 2015, vol. 29, No. 11, pp. 1066-1067 (2 pages total).

Liu, Zhigang et al., "Expression and Clinical Significance of WT1 and MRP Genes in Childhood Acute Lymphoblastic Leukemia", China Academic Journal Electronic Publishing House, 2008, pp. 195 (3 pages total).

Li, Wei et al., "Molecular Diagnostics", China Medical Science Press, Sep. 2015, pp. 70-72 (11 pages total).

Shuan Yin, "Quantitative Analysis of WT1 Gene in MRD Detection of Acute Leukemia in Children", Chinese Master's Theses Full-text Database (Medicine and Health Sciences), 2013, Issue S (24 pages total).

* cited by examiner

METHOD FOR ASSISTING DETERMINATION OF HEMATOLOGICAL STAGE OF CHILDHOOD ACUTE LYMPHOBLASTIC LEUKEMIA

CROSS REFERENCE TO RELATED APPLICATIONS

This application is a National Stage of International Application No. PCT/JP2017/025913 filed on Jul. 18, 2017, which claims priority from Japanese Patent Application No. 2016-141793 filed on Jul. 19, 2016.

TECHNICAL FIELD

The present invention relates to a method for assisting in determining the hematological stage of childhood acute lymphoblastic leukemia. Specifically, the present invention relates to a method used for distinguishing between the non-remission phase and the remission phase of acute lymphoblastic leukemia in a child test subject with acute lymphoblastic leukemia or with suspected acute lymphoblastic leukemia. The present invention also relates to an in-vitro diagnostic pharmaceutical product effectively used for assisting in determining the hematological stage of acute lymphoblastic leukemia, in particular, assisting in determining a transition from the non-remission phase to the remission phase and assisting in determining a transition from the remission phase to the non-remission phase, or monitoring the hematological stage of acute lymphoblastic leukemia.

BACKGROUND ART

A kit for measuring the WT1 mRNA level using human peripheral blood or bone marrow fluid as a test sample (a kit for measuring WT1 mRNA) is approved for use as a monitoring marker for minimal residual disease (hereinafter also referred to as "MRD") in patients with acute myeloid leukemia (hereinafter also referred to as "AML") or for use as a diagnostic aid and a monitoring marker for progression in patients with myelodysplastic syndrome (hereinafter also referred to as "MDS"), and is covered by insurance as an in-vitro diagnostic pharmaceutical product (see, for example, Non-patent Literature 1 and Patent Literature 1).

WT1 mRNA has been reported to be also expressed in acute lymphoblastic leukemia (hereinafter also referred to as "ALL") (see Non-patent Literature 2 to 8). Here, ALL is a hematopoietic neoplasm characterized by a neoplastic change and bone-marrow infiltration of immature lymphoid cells. In the WHO Classification, 4th ed., hematologic neoplasms are broadly divided into two groups with a focus on the origin of blasts: myeloid neoplasms and lymphoid neoplasms; lymphoid neoplasms are further divided into B-cell neoplasms and T-cell neoplasms; among them, ALL is positioned as an immature lymphoid neoplasm and classified into three groups as shown in Table 1 (see Non-patent Literature 9).

TABLE 1

Type of ALL according to the WHO Classification, 4th ed.

1. B-cell lymphoblastic leukemia/lymphoma, not otherwise specified
2. B-cell lymphoblastic leukamia/lymphoma, with recurrent genetic abnormalities
    1) B-ALL with t(9; 22) (q34; q11.2); BCR-ABL1
    2) B-ALL with t(v; 11q23); MLL rearranged TABLE 1-continued Type of ALL according to the WHO Classification, 4th ed.

3) B-ALL with t(12; 21) (p13; q22); TEL-AML1 (ETV6-RUNX1)
    4) B-ALL with hyperdiploidy
    5) B-ALL with hypodiploidy
    6) B-ALL with t(5; 14) (q31; q32); IL3-IGH
    7) B-ALL with t(1; 19) (q23; p13.3); E2A-PBX1 (TCF3-PBX1)
3. T-cell lymphoblastic leukemia/lymphoma From the test results of Non-patent Literature 2 to 8, WT1 mRNA in bone marrow fluid or peripheral blood of adult patients with ALL is believed to serve as a useful monitoring marker for MRD of the adult patients with ALL as in the case of AML.

Examples of methods for evaluating and measuring MRD in patients with ALL include chimeric gene quantification, MRD analysis using immune receptor (immunoglobulin/T cell receptor, Ig/TCR) gene rearrangement, MRD analysis by flow cytometry (hereinafter also referred to as "FCM"), and the like. However, the frequency of the expression of even minor BCR/ABL, which is thought to have the highest expression frequency, is as low as about 25% in adult ALL and about 3% in child ALL; therefore, cases for which such a chimeric gene, even if other chimeric genes are combined, can be used as a marker for monitoring MRD are limited. MRD analysis using Ig/TCR gene rearrangement and MRD analysis by FCM are costly and require professional skill and experience. These measurement methods are thus only conducted in some medical (research) institutions.

Meanwhile, the importance of the MRD amount after the start of treatment is acknowledged in recent years. For example, Non-patent Literature 10 indicates that WT1 mRNA has been reported to be highly expressed in many leukemias and that WT1 mRNA quantification is useful in a prognosis prediction factor and tracing of MRD in adult leukemia. However, no conclusions have been reached regarding the usefulness of WT1 mRNA quantification in a prognosis prediction factor and tracing of MRD in childhood leukemia. Non-patent Literature 11 states that WT1 mRNA is sufficient as a monitoring marker for MRD in adult patients with AML, but insufficient as a monitoring marker for MRD in patients with child ALL. The reason for this is unclear; however, it is considered that adult ALL and child ALL are different diseases from, for example, the following facts: adult patients with ALL and patients with child ALL have various genetic abnormalities whose frequency differs; and they have different prognosis (Non-patent Literature 12 to 13). In patients with child ALL, many non-neoplastic cells that express WT1 are present due to, for example, administration of granulocyte-colony stimulation factor (G-CSF) to enhance neutrophil function, or appearance of juvenile cells in peripheral blood; this is also considered to be a reason (Non-patent Literature 10).

Thus, there is a need for an index and/or standard for the diagnosis of child ALL that is different from that for the diagnosis of adult ALL.

CITATION LIST

Non-Patent Literature

NPL 1: Package insert of Wilms' tumor-1 gene (WT1) mRNA kit "WT1 mRNA Assay Kit II Otsuka" (Otsuka Pharmaceutical Co., Ltd.) (revised in July 2015 (3rd ed.)
NPL 2: Chiusa L, di Celle P F, Campisi P, Ceretto C, Marmont F, Pich A. Prognostic value of quantitative analysis of WT1 gene transcripts in adult acute lymphoblastic leukemia Haematologica. 2006; 91: 270-1.

NPL 3: Boublikova L, Kalinova M, Ryan J, Quinn F, O'Marcaigh A, Smith O, et al. Wilms' tumor gene 1 (WT1) expression in childhood acute lymphoblastic leukemia: a wide range of WT1 expression levels, its impact on prognosis and minimal residual disease monitoring. Leukemia 2006; 20: 254-63.

NPL 4: Shabani M, Asgarian-Omran H, Vossough P, Vossough P, Sharifian R A, Faranoush M, et al. Expression profile of orphan receptor tyrosine kinase (ROR1) and Wilms' tumor gene 1 (WT1) in different subsets of B-cell acute lymphoblastic leukemia. Leuk Lymphoma 2008; 49(7): 1360-7.

NPL 5: Chen J S, Hsiao C C, Sheen J M, Cheng C N. Comparison of minimal residual disease (MRD) estimated by flow cytometry and by real-time quantitative PCR of Wilms tumor gene 1 (WT1) transcript expression in children with acute lymphoblastic leukemia. Leukemia Research 2007; 31: 1351-7.

NPL 6: Busse A, Gokbuget N, Siehl J M, Hoelzer D, Schwartz S, Rietz A, et al. Wilms' tumor gene 1 (WT1) expression in subtypes of acute lymphoblastic leukemia (ALL) of adults and impact on clinical outcome. Ann Hematol 2009; 88: 1199-205.

NPL 7: Hu S Y, Gu W Y, Chen Z X, Wang X L, Cen J N, He H L, et al. The significance of detecting WT1 expression in childhood acute leukemias. Pediatric Hematology and Oncology. 2010; 27: 581-91.

NPL 8: Xu B, Song X, Yip N C, Xiao P, Zhang Y, Wang W, et al. Simultaneous detection of MDR1 and WT1 gene expression to predict the prognosis of adult acute lymphoblastic leukemia. Hematology. 2010; 15(2): 74-80.

NPL 9: Borowitz M J, Chan J K C. Precusor Lymphoid Neoplasms, overview. In: Swerdlow S H, Campo E, Harris N L, et al. eds. WHO Classification of Tumours of Haematopoietic and Lymphoid Tissues. Fourth Edition, Lyon, IARC Press 2008; 168-78.

NPL 10: Tomohei Nakao, Non-malignant elevation of Wilms tumor gene (WT1) expression is frequently observed in the blood and bone marrow of childhood acute leukemia in remission and in benign blood diseases. Doctoral (medicine) dissertation, the University of Tsukuba (Kou No. 5112). 2009: 638-640.

NPL 11: R. Zhang, et al., Comparison of minimal residual disease (MRD) monitoring by WT1 quantification between childhood acute myeloid leukemia and acute leukemia. European Review for Medical and Pharmacological Sciences 2015; 19: 2679-2688.

NPL 12: Pui C H, Relling M V, James R, Downing J R. Acute Lymphoblastic Leukemia. N Engl J Med. 2004; 350: 1535-8.

NPL 13: Noriko Usui, The Japanese journal of clinical hematology. 2009; 50: 230-43.

Patent Literature

PTL 1: WO 2014/115779 A1

SUMMARY OF INVENTION

Technical Problem

In view of the problem in the art, an object of the present invention is to provide a method for assisting in determining the hematological stage of, among all ALL cases, child ALL, in particular a method for distinguishing between the remission phase and the non-remission phase in a patient with child ALL or a patient with suspected child ALL, using WT1 mRNA as a monitoring marker for MRD. Another object of the present invention is, in particular, to provide such a method that enables simpler, easier, and much more precise determination as much as possible, than conventional methods. Additionally, another object of the invention is to provide an in-vitro diagnostic pharmaceutical product for detecting the hematological stage of ALL, in particular the remission phase, for use in performing the assisting method.

Solution to Problem

The present inventors conducted extensive research to achieve the objects, and surprisingly found that a patient with child ALL in the remission phase can be clearly distinguished from a patient with child ALL in the non-remission phase by using WT1 mRNA levels, which have been considered to be unsatisfactory as a monitoring marker for MRD of child ALL, and by using an index value calculated from the ratio of the WT mRNA level to the GAPDH mRNA level, which is used as a normalized gene (WT1 mRNA level/GAPDH mRNA level); the inventors then found that the hematological stage of child ALL, in particular, the distinction between the remission phase and the non-remission phase (diagnosis) is possible.

Further research was conducted on the basis of this finding, and then the present invention was completed. The present invention includes the following aspects.

(I) Method for Assisting in Determining Hematological Stage of Child ALL (I-1) A method for assisting in determining a hematological stage of childhood acute lymphoblastic leukemia (child ALL), the method comprising the steps of:

(1) obtaining an mRNA level of Wilms' tumor-1 gene (WT1) in a biological sample of a test subject;

(2) obtaining an mRNA level of glyceraldehyde-3-phosphate dehydrogenase (GAPDH) in the biological sample; and (3) calculating an index value necessary for assisting in the determination based on a ratio of the WT1 mRNA level obtained in step (1) to the GAPDH mRNA level obtained in step (2).

The hematological stage of child ALL is classified into two broad categories: a non-remission phase (including an untreated phase, a post-treatment recurrence phase, and a refractory phase) and a remission phase. When the method targets a patient with child ALL who has been treated with remission-induction therapy or post-remission therapy, the invention described above is also rephrased as "a method for assisting in distinguishing between the non-remission phase and the remission phase in a patient with child ALL." When the method targets a patient with suspected child ALL, the method is also rephrased as "a method for assisting in determining the presence or absence of child ALL in a patient with suspected child ALL, that is, a method for assisting in determining whether the patient is in the untreated phase of child ALL (affected) or not (not affected)."

(I-2) The method according to (I-1), wherein step (1) is a step of measuring the WT1 mRNA level using RT-PCR, or receiving the WT1 mRNA level measured using RT-PCR.

(I-3) The method according to (I-1) or (I-2), wherein step (2) is a step of measuring the GAPDH mRNA level using RT-PCR or receiving the GAPDH mRNA level measured using RT-PCR.

(I-4) The method according to (I-3), wherein one-step RT-PCR in steps (1) and (2) causes a reverse transcription reaction and an extension reaction of WT1 mRNA and GAPDH mRNA to continuously proceed in the biological sample of a test subject simultaneously in the same container.
(I-5) The method according to any one of (I-2) to (I-4), wherein the RT-PCR is two-step RT-PCR or one-step RT-PCR.
(I-6) The method according to any one of (I-2) to (I-4), wherein the RT-PCR is one-step RT-PCR.
(I-7) The method according to any one of (I-1) to (I-6), wherein the index value calculated in step (3) is a value obtained by normalizing the ratio of the WT1 mRNA level obtained in step (1) to the GAPDH mRNA level obtained in step (2) (WT1 mRNA level/GAPDH mRNA level).
(I-8) The method according to (I-7), wherein the normalization is performed by multiplying the ratio of the WT1 mRNA level to the GAPDH mRNA level (WT1 mRNA level/GAPDH mRNA level) with an average value of GAPDH mRNA levels contained in 1 μg RNA of healthy adults.
(I-9) The method according to (I-8), wherein the average value of GAPDH mRNA levels contained in 1 μg RNA of healthy adults is $2.7 \times 10^7$ copies/μg RNA.
(I-10) The method according to any one of (I-1) to (I-9), further comprising the step of:
(4) comparing the index value calculated in step (3) with a predetermined cutoff value (reference value) to show the hematological stage of the test subject based on the comparison of the values.
(I-11) The method according to (I-10), wherein step (4) is a step of showing that the test subject is in a remission phase when the index value calculated in step (3) is smaller than the predetermined cutoff value, or that the test subject is in a non-remission phase (a untreated phase, a post-treatment recurrence phase, or a refractory phase) when the index value calculated in step (3) is equal to or larger than the predetermined cutoff value.
(I-12) The method according to (I-11), wherein the non-remission phase is an untreated phase.
(I-13) The method according to any one of (I-10) to (I-12), wherein the cutoff value is determined based on a receiver operating characteristic curve (ROC curve) prepared from a correlation of the index value obtained based on the ratio of the WT1 mRNA level to the GAPDH mRNA level of the biological sample of a patient with child ALL or a patient with suspected child ALL with a hematological stage of child ALL.
(I-14) The method according to any one of (I-10) to (I-13), wherein the determination of the hematological stage of child ALL is to distinguish between the non-remission phase (the untreated phase, the post-treatment recurrence phase, or the refractory phase) of child ALL and the remission phase of child ALL; and the cutoff value is a value determined by statistical analysis of both groups of patients with child ALL in the non-remission phase (a group in the non-remission phase) and patients with child ALL in the remission phase (a group in the remission-phase).
(I-15) The method according to (I-14), wherein the statistical analysis is ROC analysis, discriminant analysis, or univariate analysis.
(I-16) The method according to any one of (I-1) to (I-15), wherein the biological sample of a test subject is blood (preferably peripheral blood) or bone marrow fluid.
(I-17) The method according to any one of (I-10) to (I-16), wherein the cutoff value is larger than the lower detection limit of the index value (the lowest detectable limit).
(I-18) The method according to any one of (I-10) to (I-17), wherein the cutoff value is larger than 50 copies/μg RNA.
(I-19) The method according to any one of (I-10) to (I-18), wherein the cutoff value is 220 copies/μg RNA for peripheral blood that is the biological sample, and 1,820 copies/μg RNA for bone marrow fluid that is the biological sample.
(I-20) The method according to any one of (I-2) to (I-19), wherein the one-step RT-PCR in step (1) uses, for the measurement of the WT1 mRNA level, (a) a primer set comprising a forward PCR primer that contains the base sequence represented by SEQ ID NO: 2 and a reverse PCR primer that contains the base sequence represented by SEQ ID NO: 3; or (b) a primer set comprising a forward PCR primer that contains the base sequence represented by SEQ ID NO: 5 and a reverse PCR primer that contains the base sequence represented by SEQ ID NO: 6.
(I-21) The method according to any one of (I-2) to (I-19), wherein the one-step RT-PCR in step (1) uses, for the measurement of the WT1 mRNA level, (a') a primer set comprising a forward PCR primer that contains the base sequence represented by SEQ ID NO: 2 and a reverse PCR primer that contains the base sequence represented by SEQ ID NO: 3, and a labeled probe that contains the base sequence represented by SEQ ID NO: 4; or (b') a primer set comprising a forward PCR primer that contains the base sequence represented by SEQ ID NO: 5 and a reverse PCR primer that contains the base sequence represented by SEQ ID NO: 6, and a labeled probe that contains the base sequence represented by SEQ ID NO: 7.
(I-22) The method according to any one of (I-3) to (I-21), wherein the one-step RT-PCR in step (2) uses, for the measurement of the GAPDH mRNA level, (c) a primer set comprising a forward PCR primer that contains the base sequence represented by SEQ ID NO: 9 and a reverse PCR primer that contains the base sequence represented by SEQ ID NO: 10 or 12.
(I-23) The method according to any one of (I-3) to (I-21), wherein the one-step RT-PCR in step (2) uses, for the measurement of the GAPDH mRNA level, (c') a primer set comprising a forward PCR primer that contains the base sequence represented by SEQ ID NO: 9 and a reverse PCR primer that contains the base sequence represented by SEQ ID NO: 10 or 12, and a labeled probe that contains the base sequence represented by SEQ ID NO: 11.
(I-24) The method according to any one of (I-3) to (I-23), wherein the one-step RT-PCR in step (1) uses, for the measurement of the WT1 mRNA level, (a') a primer set comprising a forward PCR primer that contains the base sequence represented by SEQ ID NO: 2 and a reverse PCR primer that contains the base sequence represented by SEQ ID NO: 3, and a labeled probe that contains the base sequence represented by SEQ ID NO: 4, or (b') a primer set comprising a forward PCR primer that contains the base sequence represented by SEQ ID NO: 5 and a reverse PCR primer that contains the base sequence represented by SEQ ID NO: 6, and a labeled probe that contains the base sequence represented by SEQ ID NO: 7; and the one-step RT-PCR in step (2) uses, for the measurement of the GAPDH mRNA level, (c') a primer set comprising a forward PCR primer that contains the base sequence represented by SEQ ID NO: 9 and a reverse PCR primer that contains the base sequence represented by SEQ ID NO: 10 or 12, and a labeled probe that contains the base sequence represented by SEQ ID NO: 11.

(I-25) The method according to any one of (I-1) to (I-24), wherein the WT1 mRNA level is a WT1 mRNA level in RNA extracted from peripheral white blood cells or bone-marrow-fluid nucleated cells.
(I-26) The method according to any one of (I-1) to (I-25), wherein the WT1 mRNA level in the biological sample is a monitoring marker for minimal residual disease of child ALL.
(I-27) The method according to any one of (I-1) to (I-26), wherein the test subject is a patient with child ALL or a child with suspected child ALL.
(I-28) The method according to any one of (I-1) to (I-27), wherein the biological sample is peripheral blood, preferably peripheral white blood cells, or bone marrow fluid, and preferably bone-marrow-fluid nucleated cells.
(II) Reagent Kit for Real-Time PCR for Measuring WT1 mRNA Level of Test Subject of Acute Lymphocytic Leukemia (ALL) (In-Vitro Diagnostic Pharmaceutical Product)
(II-1) A real-time PCR kit for measuring a WT1 mRNA level of a test subject of ALL, the kit comprising (a) a primer set comprising a forward PCR primer that contains the base sequence represented by SEQ ID NO: 2 and a reverse PCR primer that contains the base sequence represented by SEQ ID NO: 3; or (b) a primer set comprising a forward PCR primer that contains the base sequence represented by SEQ ID NO: 5, and a reverse PCR primer that contains the base sequence represented by SEQ ID NO: 6.
(II-2) A real-time PCR kit for measuring a WT1 mRNA level of a test subject of ALL, the kit comprising (a') a primer set comprising a forward PCR primer that contains the base sequence represented by SEQ ID NO: 2 and a reverse PCR primer that contains the base sequence represented by SEQ ID NO: 3, and a labeled probe that contains the base sequence represented by SEQ ID NO: 4; or (b') a primer set comprising a forward PCR primer that contains the base sequence represented by SEQ ID NO: 5 and a reverse PCR primer that contains the base sequence represented by SEQ ID NO: 6, and a labeled probe that contains the base sequence represented by SEQ ID NO: 7.
(II-3) The real-time PCR kit for measuring a WT1 mRNA level of a test subject of ALL according to (II-1) or (II-2), the kit further comprising (c) a primer set comprising a forward PCR primer that contains the base sequence represented by SEQ ID NO: 9 and a reverse PCR primer that contains the base sequence represented by SEQ ID NO: 10 or 12.
(II-4) The real-time PCR kit for measuring a WT1 mRNA level of a test subject of ALL according to (II-1) or (II-2), the kit further comprising (c') a primer set comprising a forward PCR primer that contains the base sequence represented by SEQ ID NO: 9 and a reverse PCR primer that contains the base sequence represented by SEQ ID NO: 10 or 12, and a labeled probe that contains the base sequence represented by SEQ ID NO: 11.
(II-5) The real-time PCR kit for measuring a WT1 mRNA level of a test subject of ALL according to any one of (II-1) to (II-4), which is a real-time PCR kit for children.
(II-6) A commercial package comprising the real-time PCR kit for measuring a WT1 mRNA level of a test subject of ALL according to any one of (II-1) to (II-5), and a manual for the kit, wherein the manual and/or the commercial package includes at least one of the following descriptions or a description related to the at least one of the following descriptions:
(i) the kit can be used for assisting in determining a hematological stage of ALL; and
(ii) a cutoff value for assisting in determining a hematological stage of ALL (reference value).
(II-7) The commercial package according to (II-6), wherein the cutoff value is larger than 50 copies/µg RNA.
(II-8) The commercial package according to (II-6) or (II-7), wherein the cutoff value is determined based on an receiver operating characteristic (ROC) curve prepared from a correlation of an index value obtained based on the ratio of the WT1 mRNA level to the GAPDH mRNA level of the biological sample of a patient with child ALL or a patient with suspected child ALL with a hematological stage of child ALL.
(II-9) The commercial package according to any one of (II-6) to (II-8), wherein the cutoff value for a patient with child ALL is 220 copies/µg RNA for peripheral blood, or 1,820 copies/µg RNA for bone marrow fluid.
(III) Method for Tracing Hematological Stage of Acute Lymphocytic Leukemia (ALL) Over Time (Monitoring Method)
(III-1) A method for tracing a hematological stage of child ALL over time (monitoring method), the method using the method for assisting in determining a hematological stage of child ALL of any one of (I-1) to (I-28).
(III-2) The method according to (III-1), wherein the tracing a hematological stage of child ALL is for tracing a transition from the non-remission phase (an untreated phase, a post-treatment recurrence phase, or a refractory phase) to the remission phase, and/or a transition from the remission phase to the non-remission phase (an untreated phase, a post-treatment recurrence phase, or a refractory phase).
(IV) Computer Program
(IV-1) A computer program configured to cause a computer to execute the steps of:
(I) receiving an input of a WT1 mRNA level in a biological sample of a test subject, and an input of a GAPDH mRNA level in the same biological sample, and
(II) calculating an index value necessary for assisting in determining a hematological stage of child ALL based on a ratio of the WT1 mRNA level that has been input in step (I) to the GAPDH mRNA level that has been input in step (I).
(IV-2) The computer program according to (IV-1), further comprising a program configured to cause the computer to execute the step of:
(III) determining the hematological stage of child ALL of the test subject based on the index value calculated in step (II).
(V) Computer Program System
(V-1) A computer system for use in determining a hematological stage of child ALL, the computer system comprising a computer that includes a processor and a memory, the memory having a computer program recorded thereon, the computer program being configured to cause the computer to execute the steps of:
(I) receiving an input of a WT1 mRNA level in a biological sample of a test subject, and an input of a GAPDH mRNA level in the same biological sample, and
(II) calculating an index value necessary for assisting in determining a hematological stage of child ALL based on a ratio of the WT1 mRNA level that has been input in step (I) to the GAPDH mRNA level that has been input in step (I).
(V-2) The computer system according to (V-1), wherein the computer program recorded on the memory further causes the computer to execute the step of:
(III) determining the hematological stage of child ALL of the test subject based on the index value obtained in step (II).

Advantageous Effects of Invention

The method assisting in determining the hematological stage of child ALL and the real-time PCR kit for measuring the WT1 mRNA level of a test subject of ALL (in-vitro diagnostic pharmaceutical product) according to the present invention enable simple detection of the hematological stage of child ALL (distinction between the remission phase and the non-remission phase (an untreated phase, a post-treatment recurrence phase, or a refractory phase), in particular distinction between the remission phase and the untreated phase) or the presence or absence of child ALL in a patient with child ALL or a child patient with suspected ALL. The real-time PCR kit according to the present invention can also detect the same in an adult patient with ALL. Additionally, the results obtained by the method according to the present invention can also be effectively used, as a piece of information for decision making, when the presence or absence of ALL and the hematological stage of ALL (in particular, the transition from the untreated phase to the remission phase) are confirmed on the basis of other related test results, such as a hemogram, myelogram, and chromosomal abnormality, and clinical symptoms.

It has been particularly essential to use bone-marrow puncture in which a fine needle is inserted into the sternum or ilium to aspirate bone marrow fluid, in order to make a definite diagnosis of ALL; however, the method according to the present invention using peripheral blood as a test sample is less invasive, reducing physical and mental strain. Thus, the method according to the present invention can be effectively used as a preliminary diagnosis method that can be performed before making a definite diagnosis of ALL.

Additionally, the monitoring method according to the present invention can trace the hematological stage of ALL of a patient with child ALL over time. The results are reflected in appropriate treatment for the patient with child ALL, and this decreases medical expenses and physical strain of the patient with child ALL.

DESCRIPTION OF EMBODIMENTS (I) Child ALL

Figure 1:
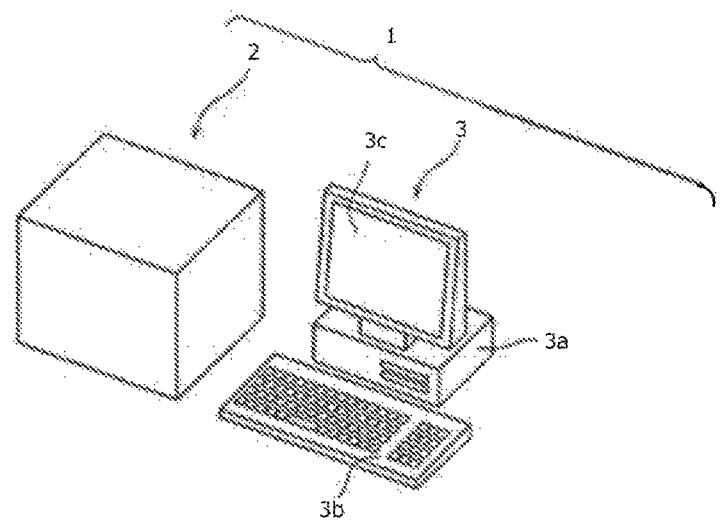
FIG. 1 is a schematic view showing an example of a determination assist device used in a method for assisting in determining the hematological stage of child ALL of the present invention.

Child ALL is a type of leukemia, typically called "blood cancer," in which lymphocytes composed of, for example, B cells and T cells among white blood cells become malignant in their immature stage, and abnormally grow, especially in the bone marrow, thus rapidly advancing the disease. The symptoms of child ALL (e.g., anemia symptom, a sense of fatigue, dizziness, wobble, palpitation, shortness of breath, swelling (e.g., edema), infection-associated fever, nose bleeding, gingival bleeding, subcutaneous bleeding, lymphadenopathy, and splenohepatomegaly) are primarily caused by the abnormal proliferation of leukemia cells (cancer cells) in the bone marrow and peripheral blood, which squeeze and decrease normal blood cells (white blood cells, red blood cells, and platelets). Although manifestation of these symptoms suggests a suspected case of child ALL, bone-marrow puncture is essential for making a definite diagnosis. When lymphoblasts that are esterase-stain negative and peroxidase-stain negative (here, the benchmark for "negative" is less than 3%) account for 25% or more of all nucleated cells in the bone marrow fluid specimen obtained by bone-marrow puncture, the case is diagnosed as having child ALL. Unlike adult ALL cases, whose long-term survival rate is less than 30 to 40%, 80% or more of child ALL cases are generally cured by treatment. This appears to be due to the lower incidence of Philadelphia chromosome mutation or T-cell acute lymphocytic leukemia than in adult-onset cases. Thus, child ALL, including its therapeutic approach, is considered to be different from adult ALL.

An expected prognosis and an appropriate therapeutic approach are determined based on the information obtained from bone-marrow puncture (bone-marrow nucleated cell count, and the morphology, cellular surface antigen analysis (type of leukemia cells), chromosomal test, gene analysis, and pathological test).

The treatment of child ALL is broadly classified into remission-induction therapy and post-remission therapy, depending on the stage of the disease; and post-remission therapy is further classified into consolidation and maintenance. The remission-induction therapy typically takes about one month. After the patient moves into the remission phase, the patient is subsequently given post-remission therapy to maintain remission and prevent recurrence, by further decreasing the remaining leukemia cells. Thus, it is very important to assess, during the course of treatment, when the patient has achieved remission, that is, whether the stage of the disease has shifted into remission.

The "remission" in child ALL is defined as the state that satisfies the following conditions:
(1) neutrophil count is 500/μL or more without administration of G-CSF,
(2) platelet count is 80,000/μL or more, (3) blood transfusion-independent,
(4) no leukemia cells are observed in peripheral blood,
(5) clinical symptoms and clinical findings for leukemia disappeared, and
(6) lymphoblasts are present in an amount of less than 5% in bone-marrow blood, with no clear leukemia cell morphology being observed.

(II) A Method for Assisting in Determining the Hematological Stage of Child ALL

The present invention relates to a method for assisting in determining the hematological stage of child ALL.

The hematological stage of child ALL includes "untreated phase (new-onset phase)," in which remission-induction therapy has yet to be performed on child ALL; "remission phase," in which child ALL has moved to the remission phase; "post-treatment recurrence phase," in which child ALL has moved from the remission phase into the phase showing increased leukemia cells again; and "refractory phase," in which therapy does not work. The present invention relates to a method for assisting in distinguishing between the remission phase and the non-remission phase (including the untreated phase, post-treatment recurrence phase, and refractory phase) among the hematological stages in child ALL. The present invention particularly preferably relates to a method for assisting in determining the transition from the untreated phase (new-onset phase), which is the non-remission phase, into the remission phase of the hematological stages in child ALL. Specifically, the present invention relates to a supplementary method for use in determining, before making a definite diagnosis, whether a patient with child ALL who has undergone remission-induction therapy or post-remission therapy has moved into the remission phase.

The method according to the present invention can be performed by at least the following steps (1) to (3):
(1) obtaining the mRNA level of WT-1 in a biological sample of a test subject (WT1 mRNA level-obtaining step);
(2) obtaining the mRNA level of GAPDH in the same biological sample (GAPDH mRNA level-obtaining step); and
(3) calculating an index value necessary for assisting in the determination based on the ratio of the WT1 mRNA level obtained in step (1) to the GAPDH mRNA level obtained in step (2) (index value-calculating step).

In the present invention, the "index value" obtained in the index value-calculating step may be referred to as "WT1 mRNA expression level."

The following describes these steps.
(1) WT1 mRNA Level-Obtaining Step

This step is a step of obtaining the WT1 mRNA level expressed in a biological sample of a test subject.

The means and method for obtaining the WT1 mRNA level are not particularly limited, as long as the WT1 mRNA level (information) is obtained as a result of performing this step. Specifically, the WT1 mRNA level may be obtained by directly measuring it, using a biological sample of a test subject as a test material, or by directly or indirectly receiving the WT1 mRNA level measured by a third party.

The target of the present invention as a test subject is a patient who has childhood acute lymphoblastic leukemia (child ALL), or a child with suspected child ALL (who may hereinafter be referred to as "a patient with suspected child ALL"). The target is preferably a patient with child ALL, and more preferably a patient with child ALL who has started to take remission-induction therapy for child ALL. In the present invention, the "child" means a male or female individual aged 1 to 19 years.

The "patient with child ALL" refers to a child patient who has received a definite diagnosis of child ALL by performing a predetermined testing method, such as physicochemical findings, blood test, and bone-marrow puncture.

The "child with suspected child ALL" (patient with suspected child ALL) refers to an individual who has no past medical history of child ALL, and who is suspected of having ALL from clinical findings (e.g., general blood analysis, and a biochemical test of blood), clinical symptoms, etc.

The biological sample for measurement in the method according to the present invention includes biological samples containing WT1 mRNA derived from a child (a patient with child ALL or a patient with suspected child ALL), such as cells, tissues, blood, bone marrow fluid, saliva, sputum, feces, and urine, with blood and bone marrow fluid being preferable. Blood is preferably peripheral blood. More preferably, blood is peripheral white blood cells, among peripheral blood, and bone marrow fluid nucleated cells, among bone marrow fluid. The biological sample for use may also be total RNA obtained by treating a sample that is likely to contain WT1 mRNA with a known method, an mRNA-enriched RNA sample, etc. An RNA sample can be prepared using a commercially available RNA extraction kit. Preferable examples include RNA samples prepared from a white blood component in blood (preferably peripheral blood) or from nucleated cells in bone marrow fluid, using a commercially available RNA extraction kit. The RNA sample for use may be in the form of an aqueous solution, or adsorbed or immobilized on an appropriate solid phase. The RNA sample may be prepared such that the mRNA level is 0.01 ng to 1 µg per 100 µL of a reaction mixture.

The WT1 gene, which is the measurement target in the present invention, is, as previously described, a gene that consists of 3037 bp identified as being responsible for child Wilms' tumor, and registered with the NCBI as "*Homo sapiens* Wilms tumor 1 (WT1), transcript variant D, mRNA" (NM_024426.4). The base sequence of the WT1 gene is shown as SEQ ID NO: 1 in a sequence listing.

The method for measuring the WT1 mRNA level in a biological sample is a method capable of measuring the mRNA level that is the transcript of the WT1 gene, and examples of the method include those widely known in the art, such as RT-PCR (two-step RT-PCR, one-step RT-PCR), in situ RT-PCR, and next-generation sequencing. The method is preferably two-step RT-PCR or one-step RT-PCR, and more preferably a measurement method using one-step RT-PCR, in which reverse transcription reaction and PCR reaction (extension and amplification) are continuously performed in the same container.

The reaction buffer for one-step RT-PCR usable in the present invention is a water-soluble buffer suitable for an enzyme having reverse transcription activity to exhibit the activity, and is, for example, a buffer with a pH of 7 to 10, and preferably 8 to 9. Examples of such buffers include tris buffers. The reaction buffer may further contain various ions necessary for the activity of an enzyme having reverse transcription activity or DNA polymerase activity. In particular, Na ions or K ions may be added in the form of salt at a concentration of 5 to 50 mM. Mg ions or Mn ions may also be added in the form of salt at a concentration of 1 to 10 mM. The buffer may further optionally contain an agent that promotes or stabilizes the activity of an enzyme having reverse transcription activity or DNA polymerase, such as a surfactant, bovine serum albumin (BSA), or gelatin. Additionally, the buffer may also contain a ribonuclease inhibitor for reducing the degradation of RNA and RNA competitors in the sample.

Examples of enzymes having reverse transcription activity include avian myeloblastosis virus-derived reverse transcriptase (AMV), Rous-associated virus-derived reverse transcriptase (RAV2), Moloney murine leukemia virus-derived reverse transcriptase (MMLV), *Thermus thermophilus*-derived DNA polymerase (Tth), *bacillus* caldotenax-derived DNA polymerase (Bca), and derivatives thereof. Of these, Tth is most suitable for the present invention. Specific examples of Tth include DNA polymerases of thermostable enzymes derived from *Thermus* species Z05. These enzymes may be those obtained by purification from their original sources or recombinant proteins produced by using genetic engineering techniques.

Four deoxynucleotide triphosphates (dATP, dCTP, dGTP, and dTTP; in the present specification, these four deoxynucleotide triphosphates may be collectively referred to as "dNTPs"), as substrates in cDNA synthesis and PCR, are added to the reaction mixture. All or a portion of dNTPs may be modified and/or replaced with labeled dNTPs to the extent that a DNA strand synthesized from a primer can extend.

The primers for use in cDNA synthesis (reverse transcription and extension reactions) from the target RNA in the present invention are oligonucleotides having a base sequence complementary to at least the base sequence of the target RNA, and are those to anneal to the target RNA under reaction conditions applied. Such oligonucleotides have a length of, for example, 6 to 100 nucleotides, and preferably 10 to 30 nucleotides. Modified and/or labeled primers may also be used. The primers can be chemically synthesized by, for example, a known method. The primers for use in PCR allow at least amplification of DNA using cDNA derived from the target RNA as a template. Thus, the primers are oligonucleotides having a base sequence complementary to at least the base sequence of the template cDNA, and are those to anneal to the cDNA under applied reaction conditions. Such oligonucleotides preferably function as primers for DNA amplification using cDNA as a template as well as primers for synthesis of cDNA from the target RNA (reverse transcription and extension reactions).

Examples of the primer set suitably used in reverse transcription of human WT1 mRNA, which is a gene of interest of the present invention, into cDNA, extension, and amplification include a primer set A comprising (A1) forward primer and (A2) reverse primer shown in Table 2; and a primer set B comprising (B1) forward primer and (B2) reverse primer shown in Table 3. Tables 2 and 3 also show sequence-specific binding probes ((A3) probe and (B3) probe) for use in detecting amplification products of the human WT1 gene amplified with these primer sets. These probes are preferably labeled to facilitate detection of the amplification products.

TABLE 2

Primer Set: A for Amplifying WT1 mRNA and Probe

| Primer/Probe | Corresponding Gene Region | Sequence Set A | SEQ ID NO |
|---|---|---|---|
| (A1) Forward | 820-841* | CGCTATTCGCAATCAGGGTTAC | 2 |
| (A2) Reverse | 936-915* | GGATCCTCATGCTTGAATGAGT | 3 |
| (A3) Probe | 842-863* | AGCACGGTCACCTTCGACGGGA | 4 |

The single asterisk indicates a region of the human WT1 gene (NM_024426.4: SEQ ID NO: 1).

TABLE 3

Primer Set B for Amplifying WT1 mRNA and Probe

| Primer/Probe | Corresponding Gene Region | Sequence Set B | SEQ ID NO |
|---|---|---|---|
| (B1) Forward | 1214-1234* | GATAACCACACAACGCCCATC | 5 |
| (B2) Reverse | 1303-1283* | CACACGTCGCACATCCTGAAT | 6 |
| (B3) Probe | 1255-1280* | AATACACACGCACGGTGTCTTCAGAG | 7 |

The single asterisk indicates a region of the human WT1 gene (NM_024426.4: SEQ ID NO: 1).

Available methods for labeling a probe include an RI method and a non-RI method, with the non-RI method being preferable. Examples of the non-RI method include fluorescence labeling, biotinylation, and chemiluminescence, with fluorescence labeling being preferable. There is no particular limitation to the fluorescent substance as long as the substance can bind to a base moiety of a nucleic acid. Examples of the fluorescent substance include a cyanine dye (such as Cy3 or Cy5 in the Cy Dye™ series), a Rhodamine 6G reagent, FAM (6-carboxyfluorescein), and HEX (6-hexachlorofluorescein). The probes may be labelled with a quenching dye. The quenching dye is not particularly limited as long as the dye can function as a quenching dye, and is also capable of binding to a base moiety of a nucleic acid as with the fluorescent substance. Examples of the quenching dye include ATTO-540Q (ATTO-TEC GmbH).

The RNA standards (target RNA) for use in the present invention can be prepared by a known method. For example, the RNA standards can be prepared with reference to the description of Proceedings of the National Academy of Sciences of the United States of America (Proc. Natl. Acad. Sci. USA), Vol. 87, pp. 2725 to 2729 (1990); Clinical Chemistry (Clin. Chem.), Vol. 41, pp. 819 to 825 (1995); or Blood, Vol. 82, pp. 1929 to 1936 (1993).

The details are as follows. A promoter sequence that serves as an origination of a reaction of an RNA synthetase, such as T7 RNA polymerase, is added to a double-stranded DNA sequence to be amplified, thereby preparing a DNA sequence used as a template for RNA synthesis. An RNA polymerase, the double-stranded DNA containing the RNA promoter sequence, and nucleoside triphosphates are added to a reaction vessel, and a reaction is performed at 37° C. for 30 minutes to 2 hours to synthesize single stranded RNA (target RNA) that is complementary to the template DNA downstream of the RNA promoter.

There is no limitation to the reaction procedure and reaction conditions for the one-step RT-PCR usable in the present invention. The following describes an example.

For example, a reaction mixture containing dNTPs, metal ions (e.g., Mg salt and Mn salt), a ribonuclease inhibitor, an enzyme having reverse transcription activity, primers, etc., is added to a reaction vessel and kept cool at 4° C. or lower until the start of reaction. A test sample to be measured that may contain human WT1 mRNA is added to the vessel, and the mixture is reacted multiple times at 50 to 70° C., and preferably 55 to 65° C., for about 2 to about 30 minutes, and preferably about 2 to about 10 minutes to synthesize cDNA (reverse transcription reaction). Immediately afterward, heating at 90 to 99° C. for about 10 seconds to about 2 minutes is performed to denature the RNA-cDNA complex (heat denaturation). Further, 2 to 50 cycles of temperature cycle reaction, each consisting of heat denaturation at 90 to 99° C., an annealing reaction at 45 to 65° C., and a DNA extension reaction at 60 to 80° C., are performed, thereby amplifying the DNA fragment derived from the target RNA. Further, when nested PCR is performed to improve sensitivity and/or specificity, primers for the first PCR and primers for the second PCR may be added together to a reaction vessel at the beginning, and the first PCR and the second PCR may be performed in a successive manner. In this case, the amount of the primers for the first PCR must be less than the amount of the primers for the second PCR, and the amount of the primers for the first PCR is preferably 100 times less than the amount for the second PCR, or smaller.

The method described above enables simple measurement of the human WT1 mRNA level by performing one-step reaction in the same container. The method can also be performed in an even simpler manner by using a commercially available real-time RT-PCR kit, and/or a real-time PCR instrument.

However, the step of obtaining the WT1 mRNA level is not limited to this method, as long as the method can obtain at least the WT1 mRNA level in a biological sample of a test subject (e.g., a patient with child ALL or a patient with suspected child ALL) as information, as stated above. The WT1 mRNA level may be obtained by directly measuring the WT1 mRNA level of a biological sample of a test subject (a test material) as described above, or by receiving the WT1 mRNA level measured by a third party from the third party or another party as data (information).

The present invention, as described above, can use two-step RT-PCR or one-step RT-PCR in a suitable manner. Examples of two-step RT-PCR include an Otsuka kit for measuring WT1 mRNA, and the two-step RT-PCR can be performed in accordance with the procedure described in the document attached to the kit (revised in March, 2013, ver. 6). Although the Examples described below use one-step RT-PCR, a study paper reports that there is a correlation in the WT1 mRNA level (quantitative value) between the use of one-step RT-PCR and the use of two-step RT-PCR (see K. Kitamura, et al. Clinical usefulness of WT1 mRNA expression in bone marrow detected by a new WT1 mRNA assay kit for monitoring acute myeloid leukemia: a comparison with expression of WT1 mRNA in peripheral blood. Int J Hematol (2016) 103:53-62.)

(2) GAPDH mRNA Level-Obtaining Step

This step is a step of obtaining the mRNA level of GAPDH (glyceraldehyde-3-phosphate dehydrogenase) expressed in the biological sample of a test subject used in step (1).

The means and method for obtaining the GAPDH mRNA level are not particularly limited, as long as the GAPDH mRNA level (information) is obtained as a result of performing this step. Specifically, the GAPDH mRNA level may be obtained by directly measuring it, using a biological sample of a test subject as a test material, or by directly or indirectly receiving the GAPDH mRNA level of the biological sample measured by a third party.

The target biological sample is the same as the biological sample derived from the child (a patient with child ALL or a patient with suspected child ALL) whose WT1 mRNA level has been measured as described above. Examples of biological samples include, as described above, cells, tissues, blood, bone marrow fluid, saliva, sputum, feces, and urine, with blood and bone marrow fluid being preferable. Blood is preferably peripheral blood. More preferably, blood is peripheral white blood cells among peripheral blood, and bone marrow fluid nucleated cells among bone marrow fluid.

GAPDH is a gene registered with the NCBI as "*Homo sapiens* glyceraldehyde-3-phosphate dehydrogenase (GAPDH), mRNA" (NM_002046.3). GAPDH is always expressed in every cell irrespective of cell differentiation and plays an essential role in the survival of cells although this gene does not perform specialized functions. In particular, GAPDH has a low base sequence homology to the human WT1 gene to be measured, thus not competing with the human WT1 gene in amplification by RT-PCR; GAPDH is therefore suitable for use as a housekeeping gene. The base sequence of GAPDH is shown as SEQ ID NO: 8 in the sequence listing.

The method for measuring the GAPDH mRNA level of a biological sample of a test subject is a method capable of measuring the mRNA level that is the transcript of GAPDH gene, and examples of the method include those widely known in the art, such as RT-PCR (two-step RT-PCR, one-step RT-PCR), in situ RT-PCR, and next-generation sequencing. The method is preferably two-step RT-PCR or one-step RT-PCR, and more preferably a measurement method using one-step RT-PCR, in which reverse transcription reaction and PCR reaction (extension and amplification) are continuously performed in the same container. The reaction buffer for one-step RT-PCR usable in the present invention, various components added to the reaction buffer, an enzyme having reverse transcription activity, and other components are as described in "(1) WT1 mRNA Level-obtaining Step" above.

Examples of the primer set suitable for use in the reverse transcription of GAPDH mRNA into cDNA, extension, and amplification include a primer set a comprising (a1) forward primer and (a2) reverse primer shown in Table 4 and a primer set b comprising (b1) forward primer and (b2) reverse primer shown in Table 5. Tables 4 and 5 also show sequence-specific binding probes ((a3) probe and (b3) probe) for use in detecting amplification products of the human GAPDH gene amplified with these primer sets. These probes are preferably labeled to facilitate detection of the amplification products. The method for labeling a probe is as described in "(1) WT1 mRNA Level-obtaining Step."

TABLE 4

Primer Set a for Amplifying GAPDH mRNA and Probe

| Primer/Probe | Corresponding Gene Region | Sequence Set a | SEQ ID NO |
|---|---|---|---|
| (a1) Forward | 77-92** | CAGCCGAGCCACATCG | 9 |
| (a2) Reverse | 219-198** | GTCAATGAAGGGGTCATTGATG | 10 |
| (a3) Probe | 134-154** | TTGGTCGTATTGGGCGCCTGG | 11 |

The double asterisk indicates a region of the human GAPDH gene (NM_002046.3: SEQ ID NO: 8).

TABLE b

Primer Set b for Amplifying GAPDH mRNA and Probe

| Primer/Probe | Corresponding Gene Region | Sequence Set b | SEQ ID NO |
|---|---|---|---|
| (b1) Forward | 77-92** | CAGCCGAGCCACATCG | 9 |
| (b2) Reverse | 202-178** | TGATGGCAACAATATCCACTTTACC | 12 |
| (b3) Probe | 134-154** | TTGGTCGTATTGGGCGCCTGG | 11 |

The double asterisk indicates a region of the human GAPDH gene (NM_002046.3: SEQ ID NO: 8).

There is no limitation to the reaction procedure and reaction conditions of one-step RT-PCR, and the method and conditions as described in "(1) WT1 mRNA Level-obtaining Step" may be used. The method can also be performed in an even simpler manner by using a commercially available real-time RT-PCR kit, and/or a real-time PCR instrument. Accordingly, the human GAPDH mRNA level can be simply measured by one-step reaction in the same container.

However, the step of obtaining the GAPDH mRNA level is not limited to this method, as long as the method can obtain the GAPDH mRNA level in a biological sample of a test subject (e.g., a patient with child ALL or a patient with suspected child ALL), as stated above. The GAPDH mRNA level may be obtained by directly measuring the GAPDH mRNA level of a biological sample of a test subject (a test material) as described above, or by collecting the GAPDH mRNA level measured by a third party as data.

The GAPDH mRNA level-obtaining step (2) can be performed separately from the WT1 mRNA level-obtaining step (1) described above, but preferably performed simultaneously with the WT1 mRNA level-obtaining step (1). More preferably, the WT1 mRNA level-obtaining step (1) and the GAPDH mRNA level-obtaining step (2) are both a step of measuring the mRNA level of a biological sample of a test subject by one-step RT-PCR to obtain the mRNA level; and one-step RT-PCR in step (1) and step (2) allows continuous PCR reaction (including reverse transcription reaction and double-stranded cDNA synthesis) of WT1 mRNA and GAPDH mRNA to proceed simultaneously in the same container (multiplex one-step quantitative RT-PCR).

This method can be performed by adding to a single reaction vessel a reaction mixture containing a primer set comprising a forward primer and a reverse primer for WT1 gene amplification, probes for detecting the amplification products, a primer set comprising a forward primer and a reverse primer for GAPDH gene amplification, probes for detecting the amplification products, cNTPs, metal ions (e.g., Mg salt and Mn salt), a ribonuclease inhibitor, an enzyme having reverse transcription activity etc.; and performing one-step RT-PCR in accordance with the reaction procedure under reaction conditions described above.

In the reaction vessel, the following two reactions proceed, enabling the real-time, simultaneous measurement of both the increase in WT1 mRNA-derived cDNA and the increase in GAPDH mRNA-derived cDNA present in the biological sample of a test subject.

The present invention, as described above, can use two-step RT-PCR or one-step RT-PCR in a suitable manner. Examples of two-step RT-PCR include an Otsuka kit for measuring WT1 mRNA, and the two-step RT-PCR can be performed in accordance with the procedure described in the document attached to the kit (revised in March, 2013, ver. 6). Although the Examples described below use one-step RT-PCR, a study paper reports that there is a correlation in the WT1 mRNA level (quantitative value) between the use of one-step RT-PCR and the use of two-step RT-PCR (see K. Kitamura, et al. Clinical usefulness of WT1 mRNA expression in bone marrow detected by a new WT1 mRNA assay kit for monitoring acute myeloid leukemia: a comparison with expression of WT1 mRNA in peripheral blood. Int J Hematol (2016) 103:53-62.)

Reaction that Proceeds in Reaction Vessel

The following describes the use of one-step RT-PCR.

Regarding WT mRNA, first, a WT1 reverse primer that has a sequence complementary to WT1 mRNA binds to WT1 mRNA contained in a measurement sample. With this WT1 reverse primer as an origination, the first strand cDNA specific to WT1 mRNA is synthesized by DNA polymerases having reverse transcription activity. Subsequently, with a WT1 forward primer having a sequence complementary to the first strand cDNA as an origination, double-stranded cDNA is synthesized. Repeatedly performing PCR using the synthesized double-stranded cDNA as a template amplifies WT1 mRNA-derived cDNA. During this amplification process, the labeled WT1 probe (labeled WT1 probe) bound to one strand of the double-stranded cDNA is degraded by 5'-3'exonuclease activity of DNA polymerase, and the labeling substance is released from the WT1 probe, emitting a signal (e.g., fluorescence signal) derived therefrom. Measuring this signal in each amplification cycle enables real-time measurement of an increase in WT1 mRNA-derived cDNA. Such continuous reaction also occurs concurrently in GAPDH mRNA in the same manner; thus, measuring the signal derived from a labeling substance released from the labeled GAPDH probe in each amplification cycle in the same manner enables real-time measurement of an increases in GAPDH mRNA-derived cDNA. In this case, the WT1 probe and GAPDH probe are each preferably labeled with a different labeling substance (e.g., fluorescence substance).

(3) Index Value-Calculating Step

This step is a step of calculating an index value necessary for assisting in the determination based on the ratio of the WT1 mRNA level obtained in step (1) to the GAPDH mRNA level obtained in step (2).

The ratio of the WT1 mRNA level to the GAPDH mRNA level can be obtained by dividing the WT1 mRNA level (the amount of a marker gene) obtained in step (1) with the GAPDH mRNA level (the amount of a housekeeping gene) obtained in step (2) as a value of "WT1 mRNA level/GAPDH mRNA level," and the ratio refers to the number of copies of WT1 mRNA per copy of GAPDH mRNA. As used herein, "per copy" refers to a single copy of GAPDH mRNA or WT1 mRNA, or a single molecule of GAPDH mRNA or WT1 mRNA. Specifically "the number of copies of WT1 mRNA per copy of GAPDH mRNA" can be rephrased as "the number of WT1 mRNA per GAPDH mRNA" or "the number of molecules of WT1 mRNA per molecule of GAPDH mRNA."

The index value necessary for assisting in the determination according to the present invention can be calculated by further normalizing the ratio of the WT1 mRNA level to the GAPDH mRNA level obtained above (WT1 mRNA level/GAPDH mRNA level) (normalization).

The "normalization" can be performed by multiplying the ratio "WT1 mRNA level/GAPDH mRNA level" obtained above with the average GAPDH mRNA level per µg RNA (GAPDH mRNA level: copies/µg RNA) of healthy adults. As used herein, the "healthy adults" means humans aged 20 years or above whose test results of general blood analysis, a biochemical test of blood, and a general test of liver function and renal function have been determined to be normal based on the common technical knowledge in the art (including both males and females).

Specifically, in an embodiment, normalization can be performed by multiplying the ratio "WT1 mRNA level/GAPDH mRNA level" obtained above with "$2.7 \times 10^7$ copies/µg RNA," which corresponds to the average GAPDH mRNA level per µg RNA of healthy adults. The thus-obtained value can be used as an index value for assisting in the determination.

In the present invention, the index value obtained in the index value-calculating step may sometimes be referred to as the "WT1 mRNA expression level."

(4) Hematological-Stage-Determination-Assisting Step

The method according to the present invention may further comprise the step of:

(4) comparing the index value obtained in step (3) with a predetermined cutoff value to show the hematological stage of child ALL of the test subject based on the comparison of the values.

When the test subject is a patient with child ALL, step (4) determines as follows: an index value obtained in step (3) smaller than the predetermined cutoff value indicates that the test subject is in the remission phase, while an index value obtained in step (3) equal to or larger than the predetermined cutoff value indicates that the test subject is in the non-remission phase. As used herein, the non-remission phase includes the untreated phase, post-treatment recurrence phase, and refractory phase. Thus, at least one phase of the disease is selected from the untreated phase, post-treatment recurrence phase, and refractory phase, depending on which non-remission phase should be distinguished from the remission phase; and the cutoff value that suits the target non-remission phase can be used. In the present invention, the term "cutoff value" refers to a "reference value" for assisting in determining the hematological stage, and the cutoff value in this specification can be rephrased as a "reference value."

When the test subject is a patient with suspected child ALL, step (4) determines as follows: an index value obtained in step (3) smaller than the predetermined cutoff value indicates that the test subject is not affected by ALL, while an index value obtained in step (3) equal to or larger than the predetermined cutoff value indicates that the test subject is affected by ALL (the "non-remission phase" in the classification of hematological stages of child ALL).

When the test subject is a patient with child ALL (preferably a patient with child ALL who has been treated with remission-induction therapy), the cutoff value for use in this step (a cutoff value for assisting in determining the hematological stage of child ALL) is a reference value to be compared with the index value for assisting in determining whether the test subject is in the remission phase of child ALL. In other words, the cutoff value is a reference value to be compared with the index value for assisting in determining whether the test subject is in the remission phase, or in the non-remission phase (untreated phase, post-treatment recurrence phase, or refractory phase).

When the test subject is a patient with suspected child ALL, the cutoff value for use in this step is a reference value to be compared with the index value for assisting in determining whether the test subject is affected by child ALL. The state of being affected by ALL corresponds to the untreated phase of a patient with child ALL, and the state of being not affected by ALL corresponds to the remission phase of a patient with child ALL.

The cutoff value is determined, depending on the type of the biological sample of the target test subject, the hematological stage to be distinguished, the purpose of determination, etc.; accordingly, multiple values are possible. Specific examples of cutoff values include a cutoff value for assisting in determining whether a test subject is in the non-remission phase or has been moved into the remission phase, when the test subject is a patient with child ALL who has been treated with remission-induction therapy; a cutoff value for assisting in determining whether a test subject is in the remission phase or in the post-treatment recurrence phase, when the test subject is a patient with child ALL who has been treated with post-remission therapy; a cutoff value for assisting in determining whether a test subject is in the refractory phase or in the remission phase, when the test subject is a patient with child ALL who has been treated with remission-induction therapy or post-remission therapy; and a cutoff value for assisting in determining whether a test subject is in the untreated phase, that is, whether a test subject is affected by child ALL or not, when the test subject is a patient with suspected child ALL. The meaning of the term "not affected" in the phrase "affected by child ALL or not" includes the case in which a test subject is affected by a blood disease other than child ALL although not affected by child ALL, and the case in which a test subject is not affected by child ALL and also not affected by any blood diseases other than child ALL.

The cutoff value for these cases varies depending on the target biological sample of a test subject. Specifically, an individual cutoff value can be determined, for example, depending on the type of the biological sample, such as peripheral blood or bone marrow fluid.

For example, when the test subject is a patient with child ALL, the cutoff value can be determined based on the correlation between the index value determined from the ratio of the WT1 mRNA level to the GAPDH mRNA level (WT1 mRNA level/GAPDH mRNA level) of a biological sample of the patient and the hematological stage of child ALL of the patient. The index value can be determined by the method described in "(3) Index Value-calculating Step."

The following describes the details. First, the distribution or average value of the index values determined based on the ratio of the WT1 mRNA level to the GAPDH mRNA level in biological samples (e.g., peripheral blood or bone marrow fluid) (WT1 mRNA level/GAPDH mRNA level) is determined for each hematological stage of multiple patients with child ALL who have received a definite diagnosis of the hematological stage of child ALL (the untreated phase, post-treatment recurrence phase, refractory phase, and remission phase) in accordance with a common diagnostic method. Subsequently, a value capable of distinguishing (separating) the group of individuals in the remission phase (a group in the remission phase) from the group of individuals in the non-remission phase (a group in the non-remission phase) is freely determined based on the obtained distribution or average value of the index values for each hematological stage (average index value), and this value can be determined to be the cutoff value. The group in the non-remission phase includes a group in the untreated-phase, a group in the post-treatment recurrence phase, and a group in the refractory phase. More specifically, the determined value capable of distinguishing between the group in the untreated phase and the group in the remission phase serves as the cutoff value for distinguishing the group in the untreated phase from the group in the remission phase. Likewise, a value capable of separating the group in the remission phase from the group in the post-treatment recurrence phase, and a value capable of separating the group in the remission phase from the group in the refractory phase each serve as the cutoff value for distinguishing these phases.

When the test subject is a patient with suspected child ALL, the cutoff value for assisting in determining whether the test subject is affected by child ALL or not is determined as follows. First, the distribution or average value of the index values based on the ratio of the WT1 mRNA level to the GAPDH mRNA level (WT1 mRNA level/GAPDH mRNA level) in biological samples (e.g., peripheral blood or bone marrow fluid) is determined. The distribution or average value is determined based on multiple patients with child ALL who have been received a definite diagnosis of child ALL (in the untreated phase) by a common diagnostic method and multiple children who are not affected by ALL, for each case where child ALL is present or absent. Subsequently, a value capable of distinguishing (separating) between the group of children who are affected by child ALL and the group of children who are not affected by ALL is freely determined based on the obtained distribution or average value (average index value) of the index values for each case where child ALL is present or absent. The "children who are not affected by ALL" includes children who have not been affected by ALL but affected by a blood disease other than ALL, and children who have been affected by neither ALL nor any blood disease other than ALL. In particular, children who are not affected by ALL indicates children who have been affected by a blood disease other than ALL, exhibiting symptoms similar to those of ALL.

In the present invention, the cutoff value capable of distinguishing (separating) these two groups can be determined by statistical analysis. Statistical analysis available includes a variety of analysis methods. Specific examples thereof include ROC analysis, discriminant analysis, and univariate analysis.

The discriminant analysis is a means used in, for example, distinguishing two groups from some data, and is an analysis for distinguishing one group (equal or above a predetermined value) from another (less than the predetermined value).

The univariate analysis is an analysis for use in, for example, determining how a criterion has been determined as in the following case: when a dosage of a medicinal agent to reduce the blood pressure of a hypertensive patient by 10 points is considered with response variables ("Y" in Y=a+bX) as continuous data, the univariate analysis is used to analyze on what criterion the "10" points has been determined.

In the present invention, receiver operation character analysis (ROC analysis) is preferably used. The following describes how to determine a cutoff value using ROC analysis. A cutoff value capable of distinguishing (separating) the non-remission phase from the remission phase can be determined, for example, by preparing a biaxial (sensitivity and 100%-specificity), receiver operating characteristic curve (ROC curve) of the index values (values obtained by normalizing the ratio of the WT1 mRNA level to the GAPDH mRNA level) obtained from the two groups. A cutoff value based on an ROC curve can be set, for example, in accordance with the methods described in "Journal of Analytical Bio-Science," 2005, Vol. 28, pp. 133-139; and Perkins N J, Am J Epidemiol. 2006; 163: 670-675.

The method for determining a cutoff value using an ROC curve includes the following two methods: (1) a method using the distance from the upper-left corner of the graph showing an ROC curve; and (2) a method using the Youden index. In method (1), from the fact that an ROC curve of independent variable excellent in sensitivity and specificity becomes close to the upper-left corner, the point at which the distance between the curve and the upper-left corner is minimum is determined to be a cutoff value. In method (2), the point most distant from an ROC curve of independent variable that has low prediction ability and diagnostic performance (i.e., a curve with AUC being 0.500) is determined to be a cutoff value. Specifically, the equation "sensitivity+specificity−1" is calculated, and the point at which the value is largest is determined to be a cutoff value (Youden index).

As described above, a cutoff value for assisting in distinguishing groups (between a group in the remission phase and a group in the untreated phase, between a group in the remission phase and a group in the post-treatment recurrence phase, between a group in the remission phase and a group in the refractory phase, between a group of individuals affected by ALL and a group of individuals who are not affected by ALL) can be determined.

In the present invention, the cutoff value is higher than the lower detection limit of the index value. The phrase "the lower detection limit of the index value" refers to the detectable minimal level (value) of the index value, and refers specifically to the detectable minimal level measured by RT-PCR. More preferably, the lower detection limit of the index value refers to a value of the lower detection limit measurable with the capability of the real-time PCR kit according to the present invention.

In the Examples described below, among these cutoff values, a cutoff value (Youden index) for assisting in distinguishing between the untreated phase and the remission phase is set by using the ROC curve (Youden index analysis) by way of example. Specifically, when the biological sample for use is bone marrow fluid, the preferable cutoff value is 1,820 copies/μg RNA (sensitivity 58.1%, specificity 98.0%, AUC 0.794). When the biological sample for use is peripheral blood, the preferable cutoff value is 220 copies/μg RNA (sensitivity 68.8%, specificity 98.0%, AUC 0.894).

Accordingly, untreated patients with child ALL and patients with child ALL who have been treated with remission-induction therapy are supplementarily determined as to whether they are in the untreated phase or the remission phase on the basis of the cutoff value. Specifically, when a patient with child ALL exhibits an index value of less than 220 copies/μg RNA calculated using peripheral blood and/or less than 1,820 copies/μg RNA calculated using bone marrow fluid as a test sample, the patient with child ALL is determined to have moved into the remission phase (preliminary determination). Conversely, when the patient with child ALL exhibits an index value of 220 or more copies/μg RNA calculated using peripheral blood and/or 1,820 or more copies/μg RNA calculated using bone marrow fluid, the patient is determined to be still in the untreated phase (preliminary determination).

The method for assisting in determining the hematological stage of acute lymphocytic leukemia described above enables the trace of the hematological stage of a patient with child ALL over time. Thus, the present invention also relates to a method for tracing the hematological stage of child ALL over time by performing the method for assisting in determining the hematological stage of child ALL. The trace of the hematological stage of child ALL includes the trace of the transition from the non-remission phase to the remission phase, and the trace of the transition from the remission phase to the non-remission phase.

(III) Real-Time PCR Kit for Measuring WT1 mRNA Level of Test Subject of Acute Lymphoblastic Leukemia (In-Vitro Diagnostic Pharmaceutical Product)

The real-time PCR kit for measuring the WT1 mRNA level of a test subject of ALL according to the present invention comprises both a primer set for subjecting human WT1 mRNA to RT-PCR and a primer set for subjecting GAPDH mRNA as a housekeeping gene to RT-PCR. The kit may also comprise probes used for detecting amplification products of human WT1 mRNA amplified by RT-PCR and amplification products of the housekeeping gene (GAPDH mRNA) amplified by RT-PCR.

An example of the kit is one that comprises a primer set A comprising (A1) a forward primer (SEQ ID NO: 2) and (A2) a reverse primer (SEQ ID NO: 3) shown in Table 2 as a primer set for subjecting human WT1 mRNA to RT-PCR, and (A3) a probe (SEQ ID NO: 4) shown in Table 2 as a sequence-specific binding probe used for detecting amplification products of human WT1 gene amplified with the primer set, and that also comprises a primer set a comprising (a1) a forward primer (SEQ ID NO: 9) and (a2) a reverse primer (SEQ ID NO: 10) shown in Table 4 as a primer set for subjecting human GAPDH mRNA used as a housekeeping gene to RT-PCR, and (a3) a probe (SEQ ID NO: 11) shown in Table 4 as a sequence-specific binding probe used for detecting amplification products of human GAPDH gene amplified by the primer set.

The probes are preferably labeled to facilitate detection of the amplification products.

Available methods for labeling a probe include an RI method and a non-RI method. It is preferable to use a non-RI method. Examples of the non-RI method include fluorescence labeling, methods using an enzyme, biotinylation, methods using a chromophore, chemiluminescent labeling methods, and the like. Fluorescence labeling is preferable. There is no particular limitation to the fluorescent substance as long as the substance can bind to a base moiety of a nucleic acid. Examples of the fluorescent substance include a cyanine dye (such as Cy3 or Cy5 in the Cy Dye™ series), a Rhodamine 6G reagent, FAM (6-carboxyfluorescein), and HEX (6-hexachlorofluorescein). The probes may be labeled with a quenching dye. The quenching dye is not particularly limited as long as it can function as a quenching dye and is also capable of binding to a base moiety of a nucleic acid as with the fluorescent substance. Examples of the quenching dye include ATTO-540Q (ATTO-TEC GmbH).

Another example of the kit is one that comprises a primer set B comprising (B1) a forward primer (SEQ ID NO: 5) and (B2) a reverse primer (SEQ ID NO: 6) shown in Table 3 as a primer set for subjecting human WT1 mRNA to RT-PCR, and (B3) a probe (SEQ ID NO: 7) shown in Table 3 as a sequence-specific binding probe used for detecting amplification products of the human WT1 gene amplified with the primer set, and that also comprises a primer set b comprising (b1) a forward primer (SEQ ID NO: 9) and (b2) a reverse primer (SEQ ID NO: 12) shown in Table 5 as a primer set for subjecting human GAPDH mRNA used as a housekeeping gene to RT-PCR, and (b3) a probe (SEQ ID NO: 11) shown in Table 5 as a sequence-specific binding probe used for detecting amplification products of the human GAPDH gene amplified with the primer set.

The real-time PCR kit for measuring the WT1 mRNA level of a test subject of acute lymphoblastic leukemia according to the present invention may comprise not only the above components but also various components necessary for two reactions, i.e., a reverse transcription reaction and PCR (dNTPs, metal ions, buffering components for pH adjustment, etc.), an enzyme having reverse transcription activity etc., an enzyme cofactor, etc. The metal ions are not particularly limited, and, for example, salts that generate divalent metal ions, such as manganese acetate salts and magnesium acetate salts, are usable. The components of the kit may further contain a component for stabilizing an enzyme, a ribonuclease inhibitor, etc. The kit may comprise a standard solution containing a predetermined concentration of WT1 RNA and/or GAPDH RNA, and, as necessary, a buffer for diluting the standard solution.

The real-time PCR kit for measuring the WT1 mRNA level of a test subject of acute lymphoblastic leukemia according to the present invention may further comprise a container (a reaction vessel) for containing a reaction mixture or a container for maintaining or storing a test sample (e.g., a container for collecting and storing peripheral blood or bone marrow fluid). Preparing beforehand a reaction vessel in which a requisite amount of a reaction mixture for one time is dispensed makes it possible to conveniently quantify the human WT1 mRNA level because the reactions can be started by only adding a test sample to be measured. In particular, it is useful for quantifying the human WT1 mRNA level in multiple test samples. The kit may optionally comprise other components that facilitate the preparation of a test sample. The kit may also comprise one or more instruments for assisting in collecting a test sample, such as a pipette, a syringe, tweezers, or the like.

The real-time PCR kit for measuring the WT1 mRNA level of a test subject of acute lymphoblastic leukemia according to the present invention may be packaged alone or packaged with a manual for the kit as necessary, and commercially distributed. The manual may be written or may be in a computer-readable medium (such as a disk, CD, or DVD). The contents of the manual are not limited and may include, for example, regarding to the real-time PCR kit of the present invention, at least one item selected from the group consisting of the constitution of the kit, the intended use, the measurement principle, the operation method (dosage and administration), the method of determining a measurement result, and clinical significance.

The real-time PCR kit for measuring the WT1 mRNA level of a test subject of acute lymphoblastic leukemia according to the present invention encompasses a kit with which WT1 mRNA in RNA extracted from peripheral blood (white blood cells) or bone marrow fluid (nucleated cells) can be measured by quantitative real-time RT-PCR. As the intended use or clinical significance of the kit, for example, the kit can be used to assist in determining the hematological stage of ALL (remission phase or non-remission phase (untreated phase, recurrence phase after remission, or refractory phase)) of a patient with ALL or a patient with suspected ALL (assisting in the diagnosis of a patient with ALL). The real-time PCR kit can be also used to monitor ALL progression or recurrence in a patient with ALL or monitor a therapeutic effect in a patient with ALL receiving treatment. The kit for diagnosing ALL can be used to assist in determining the presence or absence of child ALL (assist in diagnosing the presence or absence of child ALL) in a patient with suspected child ALL.

The age of the user of the real-time PCR kit for measuring the WT1 mRNA level of a test subject of acute lymphoblastic leukemia according to the present invention is not particularly limited, and the kit can be used for adults and for children.

(IV) Computer Program Product

The present invention also includes a computer program product for causing a computer to carry out determination of the hematological stage of child ALL. Examples of the computer program product include a computer program that can be downloaded via, for example, the Internet, and a medium having the program recorded thereon (such as a disk, CD, or DVD).

An example is a computer program configured to cause a computer to execute, for example, the following steps:
(I) receiving an input of a WT1 mRNA level in a biological sample of a test subject and an input of a GAPDH mRNA level in the same biological sample; and
(II) calculating an index value necessary for assisting in determining a hematological stage of child ALL based on a ratio of the WT1 mRNA level to the GAPDH mRNA level that have been input in step (I). In step (I), the input of the WT1 mRNA level and the input of the GAPDH mRNA level may be received simultaneously or separately.

The program may be a program configured to cause the computer to further execute the following step (III) in addition to steps (I) and (II):
(III) determining the hematological stage of child ALL of the test subject based on the index value obtained in step (II).

Determination Assist Device for Hematological Stage of Child ALL

An embodiment of a device (computer device) suitable for executing the computer program is described below with reference to the drawings; however, the present invention is not limited to this embodiment. FIG. 1 is a schematic view showing an example of a device used for assisting in determining the hematological stage of a test subject (hereinafter also simply referred to as "determination assist device"). A determination assist device 1 shown in FIG. 1 includes a measurement device 2 and a computer system 3 connected to the measurement device 2. In this embodiment, the measurement device 2 is a device for measuring the WT1 mRNA level and/or GAPDH mRNA level in a biological sample of a test subject. The measurement device 2 obtains the WT1 mRNA level and/or GAPDH mRNA level itself in a biological sample of a test subject, or information related to the WT1 mRNA level and/or GAPDH mRNA level, such as fluorescence or luminescence intensity due to amplification products of each gene amplified by RT-PCR or the like. Specifically, when a biological sample collected from a test subject is set in the measurement device 2, the measurement device 2 obtains information related to the WT1 mRNA level and/or GAPDH RNA level in the biological sample and transmits the obtained information to the computer system 3. However, the measurement device 2 is optional in the determination assist device of the present invention; the determination assist device of the present invention may consist of the computer system 3.

The computer system 3 includes a computer body 3a, an input unit 3b including a keyboard and/or a mouse, and a display unit 3c configured to display, for example, information regarding a test subject, a test sample, etc., and a determination result. The computer system 3 receives an input of information related to the WT1 mRNA level and/or GAPDH mRNA level in a test sample. The computer system 3 executes a program for determining the hematological stage of child ALL of the test subject, based on the information.

Figure 2:
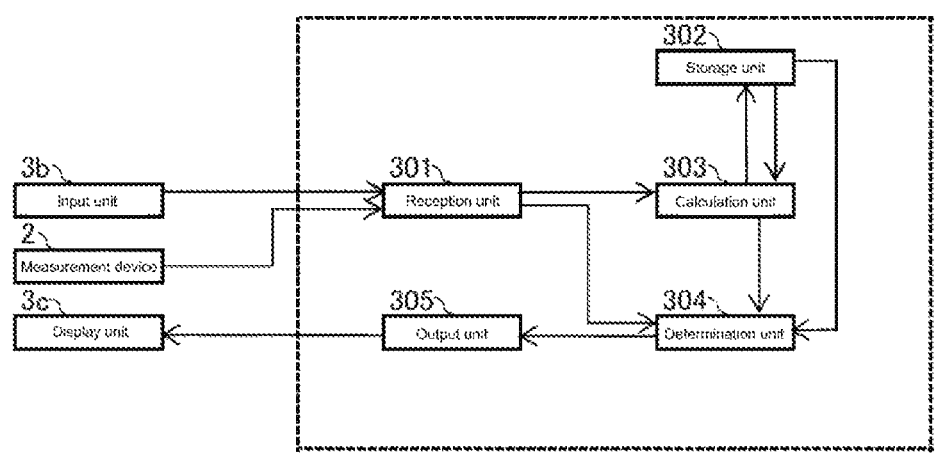
FIG. 2 is a block diagram showing the functional configuration of software of the determination assist device.

FIG. 2 is a functional block diagram showing software of the computer body 3a of the determination assist device 1. As shown in FIG. 2, the computer body 3a includes a reception unit 301, a storage unit 302, a calculation unit 303, a determination unit 304, and an output unit 305.

The reception unit 301 can receive information necessary for determining the hematological stage of child ALL, specifically information regarding a test subject, a test sample, etc., or information related to, for example, the WT1 mRNA level and/or GAPDH mRNA level in a biological sample of a test subject, via the input unit 3b. The reception unit 301 can also be communicatively connected to the measurement device 2, which is an optional device, over a network, and can receive information (e.g., information regarding a test subject, a test sample, etc., or information related to, for example, the WT1 mRNA level and/or GAPDH mRNA level in a biological sample of a test subject) transmitted from the measurement device 2.

The storage unit 302 stores a computer program for implementing the present invention in the computer system, such as formulas and/or processing programs for calculating a reference value necessary for the determination (information necessary for normalization (e.g., the average GAPDH mRNA level per µg RNA of healthy adults), a cutoff value) and for calculating the WT1 gene expression level. The calculation unit 303 calculates the ratio of the WT1 mRNA level to the GAPDH mRNA level (WT1 mRNA level/GAPDH mRNA level), an index value (WT1 mRNA expression level), etc., according to the stored formulas, using the information obtained in the reception unit 301. The determination unit 304 determines whether the index value (WT1 mRNA expression level) obtained by the reception unit 301 or calculated by the calculation unit 303 is equal to or larger than a reference value (cutoff value) stored in the storage unit 302, or less than the reference value (cutoff value). The output unit 305 outputs the determination result obtained by the determination unit 304 to the display unit 3c as a determination result of the hematological stage of child ALL of the test subject. The display unit 3c is not limited and may include a cathode-ray tube (CRT), a liquid crystal display (LCD), a plasma display panel (PDP), or an organic EL display (OLED).

Figure 3:
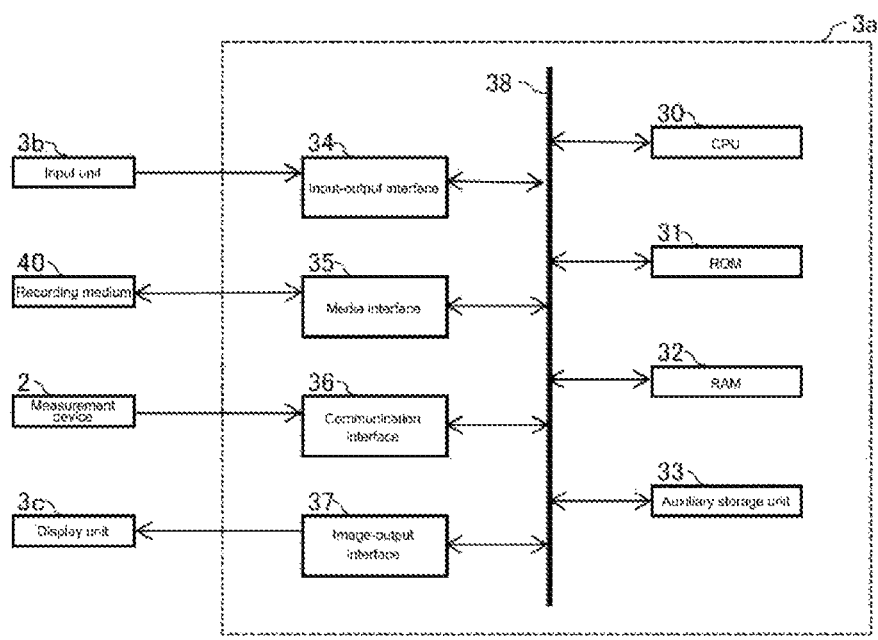
FIG. 3 is a block diagram showing the hardware configuration of the determination assist device.

FIG. 3 is a block diagram showing the hardware configuration of the computer body 3a shown in FIG. 2. As shown in FIG. 3, the computer body 3a includes a central processing unit (CPU) 30, a read only memory (ROM) 31, a RAM 32, an auxiliary storage unit 33, an input-output interface 34, a media interface 35, a communication interface 36, and an image-output interface 37. The CPU 30, the ROM 31, the RAM (random access memory) 32, the auxiliary storage unit 33, the input-output interface 34, the media interface 35, the communication interface 36, and the image-output interface 37 are connected via a bus 38 so as to enable data communication.

The CPU 30 can execute a computer program stored in the ROM 31 and a computer program loaded in the RAM 32. When the CPU 30 executes such a computer program and processes the obtained data, the individual functions shown in FIG. 2 are executed. Thereby, the computer system 3 functions as a device for determining the hematological stage of child ALL in a test subject.

The ROM 31 includes a mask ROM, PROM, EPROM, EEPROM, or the like. On the ROM 31, a computer program executed by the CPU 30 as described above and data used for the program are recorded.

The RAM 32 includes an SRAM, DRAM, or the like. The RAM 32 is used for reading computer programs recorded on the ROM 31 and the auxiliary storage unit 33. The RAM 32 is also used as a work area of the CPU 30 when these computer programs are executed.

The auxiliary storage unit 33 includes a hard disk, a semiconductor memory device such as flash memory, an optical disc, or the like. The auxiliary storage unit 33 stores an operating system, a computer program, such as an application program, to be executed by the CPU 30, and setting data used for executing the computer program.

The media interface 35 can read a computer program, data, and an application program recorded on a recording medium 40. The read application program and the like are stored in the RAM 32 or the auxiliary storage unit 33. The media interface 35 also writes information generated by the CPU 30 to the recording medium 40. The media interface 35 writes, to the recording medium 40, information generated by the CPU 30 and stored in the auxiliary storage unit 33.

The recording medium 40 includes a portable recording medium, such as a flexible disk, a CD-ROM, or a DVD-ROM. The recording medium 40 is connected to the media interface 35 by a reading device, such as a flexible disk drive, a CD-ROM drive, or a DVD-ROM drive. The recording medium 40 may store, for example, an application program for causing a computer to execute an operation.

The input-output interface 34 includes, for example, a serial interface, such as USB, IEEE1394, or RS-232C, a parallel interface, such as SCSI, IDE, or IEEE1284, and an analog interface including a D/A converter, an A/D converter, and the like. The input-output interface 34 is connected to the input unit 3b, such as a touch panel, a pen tablet, a keyboard, a mouse, or a microphone. A user can input various commands to the computer body 3a through the input unit 3b. The input-output interface 34 is also connected to the output unit 305, such as a display or a printer, and outputs information generated by the CPU 30 or information generated by the CPU 30 and stored in the auxiliary storage unit 33 to the output unit 305.

The communication interface 36 includes, for example, a serial interface, such as USB, IEEE1394, or RS-232C, a parallel interface, such as SCSI, IDE, or IEEE1284, an analog interface including a D/A converter, an A/D converter, and the like, a network interface controller, and the like. The communication interface 36 receives data from the measurement device 2 or another external device under control of the CPU 30, and transmits or displays information stored in or generated by a data processing unit, to the measurement device 2 or the outside as necessary. The communication interface 36 can also communicate with the measurement device 2 or another external device over a network. The communication interface 36 also enables the computer body 3a to transmit print data to a printer or the like.

The image-output interface 37 is connected to the display unit 3c. Therefore, the display unit 3c can output a video signal corresponding to image data provided by the CPU 30. The display unit 3c displays an image (screen) according to the input video signal.

Figure 4:
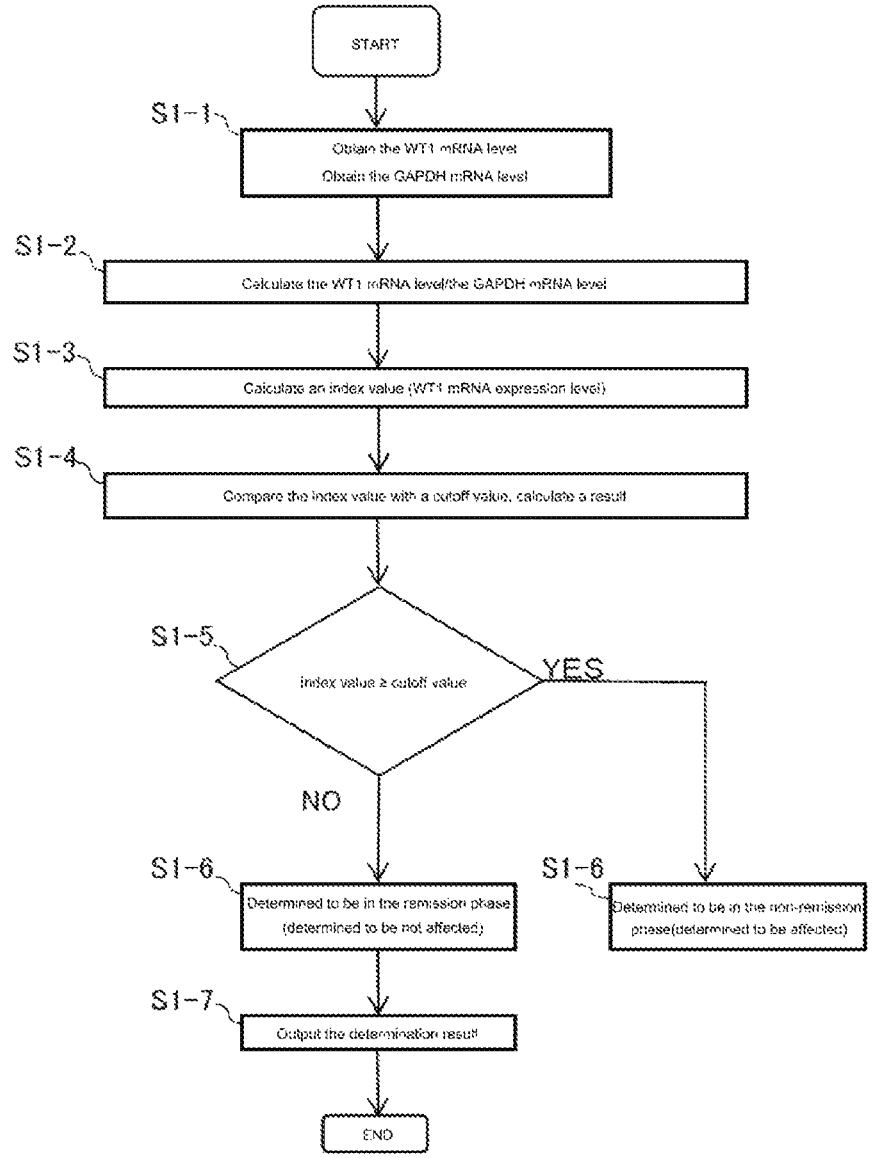
FIG. 4 shows an example of a flowchart illustrating the operation of the determination assist device.

Operation of Determination Assist Device for Determining Hematological Stage of Child ALL Using the flowchart shown in FIG. 4, the procedure for determining the hematological stage of child ALL of a test subject by the determination assist device 1 is described. Here, a case in which an index value (WT1 mRNA expression level) is calculated from the WT1 mRNA level and GAPDH mRNA level obtained using a biological sample from a test subject and it is determined whether the obtained index value is equal to or larger than a reference value (cutoff value), is described below as an example; however, the present invention is not limited to only this embodiment.

In step S1-1, the reception unit 301 of the determination assist device 1 obtains the WT1 mRNA level and GAPDH mRNA level in a biological sample of a test subject from the measurement device 2. Alternatively, in step S1-1, the WT1 mRNA level and the GAPDH mRNA level may be obtained by receiving inputs of the WT1 mRNA level and GAPDH mRNA level in a biological sample of a test subject from the input unit 3b of the determination assist device 1. The reception unit 301 may receive the input of the WT1 mRNA level and the input of the GAPDH mRNA level simultaneously or separately.

Subsequently, in step S1-2, the calculation unit 303 calculates the ratio of the WT1 mRNA level to the GAPDH mRNA level (WT1 mRNA level/GAPDH mRNA level) from the information obtained in step 1-1 (Wr1 mRNA level and GAPDH mRNA level) and, as necessary, transmits it to the storage unit 302. In step S1-3, the calculation unit 303 calculates an index value necessary for assisting in determination, based on the WT1 mRNA level/GAPDH mRNA level calculated in step S1-2 and the average GAPDH mRNA level per µg RNA of healthy adults stored in the storage unit 302.

Thereafter, in step S1-4, the determination unit 304 reads the desired (target) cutoff value from various cutoff values stored in the storage unit 302 (a cutoff value for distinguishing the remission phase from the untreated phase, a cutoff value for distinguishing the remission phase from the post-treatment recurrence phase, and a cutoff value for distinguishing the remission phase from the refractory phase) according to the purpose, compares the cutoff value with the index value of the biological sample obtained in step S1-3, and calculates whether the index value is equal to or larger than the cutoff value, or less than the cutoff value.

In steps S1-5 to S1-6, whether the hematological stage of the test subject is the remission phase (not affected) or the non-remission phase (untreated phase, post-treatment recurrence phase, refractory phase; affected) is distinguished based on the result of the calculation in step S1-4. Specifically, when the test subject is a patient with child ALL, the index value of a biological sample of the patient is compared with a cutoff value for distinguishing the remission phase from the untreated phase. When the index value is equal to or larger than the cutoff value, it is determined that the patient is in the untreated phase; and when the index value is less than the cutoff value, it is determined that the patient is in the remission phase. Moreover, when the test subject is a patient with child ALL, the index value of a biological sample of the patient is compared with a cutoff value for distinguishing the remission phase from the post-treatment recurrence phase. When the index value is equal to or larger than the cutoff value, it is determined that the patient is in the post-treatment recurrence phase; and when the index value is less than the cutoff value, it is determined that the patient is in the remission phase. Further, when the test subject is a patient with child ALL, the index value of a biological sample of the patient is compared with a cutoff value for distinguishing the remission phase from the refractory phase. When the index value is equal to or larger than the cutoff value, it is determined that the patient is in the refractory phase; and when the index value is less than the cutoff value, it is determined that the patient is in the remission phase. In addition, when the test subject is a patient with suspected child ALL, the index value of a biological sample of the patient is compared with a cutoff value for distinguishing the remission phase from the untreated phase. When the index value is equal to or larger than the cutoff value, it is determined that the patient with suspected child ALL is affected by child ALL; and when the index value is less than the cutoff value, it is determined that the patient with suspected child ALL is not affected by child ALL.

In step S1-7, the output unit 305 outputs the determination result of the hematological stage of child ALL of the test subject and displays it on the display unit 3c. Thereby, in the determination assist device 1, when the test subject is a patient with child ALL, it can be distinguished whether the hematological stage of child ALL is the remission phase or the non-remission phase (untreated phase, post-treatment recurrence phase, refractory phase); when the test subject is a patient with suspected child ALL, it can be distinguished whether the patient is affected by child ALL or not (affected or not affected). The result can be provided to physicians etc. as information to assist in determining the hematological stage of child ALL.

(IV) Computer System

The present invention also includes a computer system suitable for use in determining the hematological stage of child ALL of a test subject. The system includes a computer including a processor and a memory (the storage unit 302), the memory having a computer program recorded thereon, the computer program being for executing the following steps in the computer system:

(I) receiving an input of a WT1 mRNA level in a biological sample of a test subject, and an input of a GAPDH mRNA level in the same biological sample, and (II) calculating an index value necessary for assisting in determining a hematological stage of child ALL based on a ratio of the WT1 mRNA level to the GAPDH mRNA level that have been input in step (I).

In step (I), the input of the WT1 mRNA level and the input of the GAPDH mRNA level may be received simultaneously or separately.

The computer program may further comprise a program to execute the following step (III):

(III) determining the hematological stage of child ALL of the test subject based on the index value obtained in step (II).

According to the present embodiment, the hematological stage of child ALL of the test subject can be determined based on the result obtained in step (II) or (III). For example, when the test subject who has provided the biological sample is a patient with child ALL, a determination result of distinguishing whether the hematological stage of child ALL of the test subject is the remission phase or the untreated phase, distinguishing whether the hematological stage of child ALL of the test subject is the remission phase or the post-treatment recurrence phase, or distinguishing whether the hematological stage of child ALL of the test subject is the remission phase or the refractory phase can be provided. When the test subject who has provided the biological sample is a patient with suspected child ALL, a determination result of whether the test subject is affected by child ALL or not can be provided. These determination results can be provided to physicians etc. to thereby assist them in diagnosing the hematological stage of child ALL.

EXAMPLES

The present invention is described in detail below with reference to an Example; however, the present invention is not limited to the Example.

Example 1

The WT1 mRNA level in RNA extracted from peripheral white blood cells and bone-marrow-fluid nucleated cells was measured in patients with child ALL and children suspected of having ALL, using WT1 mRNA Assay Kit II "Otsuka" (Otsuka Pharmaceutical Co., Ltd.), which is a Wilms' tumor-1 gene (WT1) mRNA kit. The kit includes a mix solution for RT-PCR, a metal ion solution (such as manganese acetate), an RNA standard solution, which is a mixed solution of WT1 and GAPDH (such as WT1 RNA and GAPDH RNA), a diluent for the standard solution (such as a buffer), etc. The mix solution for RT-PCR contains the WT1 forward primer, WT1 reverse primer, WT1 probe, GAPDH forward primer, GAPDH reverse primer, and GAPDH probe shown in Table 5. The WT1 probe is labeled at the 5' end with HEX (6-hexachlorofluorescein), and the GAPDH probe is labeled at the 5' end with FAM (6-carboxyfluorescein). Each probe is labeled at the 3' end with ATTO-540Q (ATTO-TEC GmbH), which is a quenching dye.

TABLE 6

Primer Sets Contained in Mix Solution for RT-PCR

| Primer/probe | Corresponding Gene Region | Sequence Set | SEQ ID NO |
|---|---|---|---|
| WT1 Forward | 1214-1234* | GATAACCACACAACGCCCATC | 5 |
| WT1 Reverse | 1303-1283* | CACACGTCGCACATCCTGAAT | 6 |
| WT1 Probe | 1255-1280* | AATACACACGCACGGTGTCTTCAGAG | 7 |

| Primer/probe | Corresponding Gene Region | Sequence Set | SEQ ID NO |
|---|---|---|---|
| GAPDH Forward | 77-92-** | CAGCCGAGCCACATCG | 9 |
| GAPDH Reverse | 202-178** | TGATGGCAACAATATCCACTTTACC | 12 |
| GAPDH Probe | 134-154** | TTGGTCGTATTGGGCGCCTGG | 11 |

*means the region of human WT1 gene (NM_024426.4: SEQ ID NO: 1)
**means the region at human GAPDH gene (NM_002046.3: SEQ ID NO: 8)

The method for RNA extraction and the method for measuring and calculating the WT1 mRNA level in extracted RNA were performed according to the description of the manual (package insert) of WT1 mRNA Assay Kit II "Otsuka" (Otsuka Pharmaceutical Co., Ltd.).

(1) Test Subjects

A test was performed for a total of 49 patients from which consent was obtained for the test among untreated patients with new-onset child ALL and child patients with suspected child ALL in 14 medical institutions in Japan from December 2014 to the end of December 2015. Since one of the patients was transferred to another hospital before the completion of remission-induction therapy, specimens at two time points, after the completion of the remission-induction therapy and after the completion of early consolidation therapy, could not be collected. When a patient suspected of having ALL (patient with suspected ALL) was diagnosed with a disease other than ALL at a later date, the test was terminated at one point before the start of treatment.

(2) Test Method (Follow-Up Test: 6 Months)

The follow-up period was 4 to 6 months after the start of the treatment. At each of the following time points, 1 mL of bone marrow fluid and 7 mL of peripheral blood were collected, and WT1 mRNA in the test samples was measured (see FIG. 5).
(a) Before the start of treatment (TP 0)
(b) After the completion of remission-induction therapy (TP 1)
(c) After the completion of early consolidation therapy (TP 2)
(d) At the time of bone-marrow examination after the completion of early consolidation therapy (only the case in which bone-marrow examination was performed for medical examination)

Table 7 shows the details of specimens used for analysis among those of the 49 patients.

TABLE 7

Details of Specimens Used for Analysis

| Specimen collection point | Peripheral blood | Bone marrow fluid | Total |
|---|---|---|---|
| TP0 (before start of treatment) | 48 | 43 | 91 |
| TP1 (after completion of remission-induction therapy) | 48 | 47 | 95 |
| TP2 (after completion of early consolidation therapy) | 48 | 47 | 95 |
| TP2 to test end date | 5 | 5 | 10 |
| Total | 149 | 142 | 291 |

(3) Test Results (3-1) Changes in WT1 mRNA Expression Level (Index Value) During Follow-Up Excluding one patient who was transferred to another hospital in the course of the test, 48 of the 49 patients were followed every month for 4 to 6 months after the start of the treatment. The results reveal that the hematological stage was the remission phase at all of the follow-up points other than before the start of the treatment (TP0), in all of the 48 patients.

Figures 5, 6:
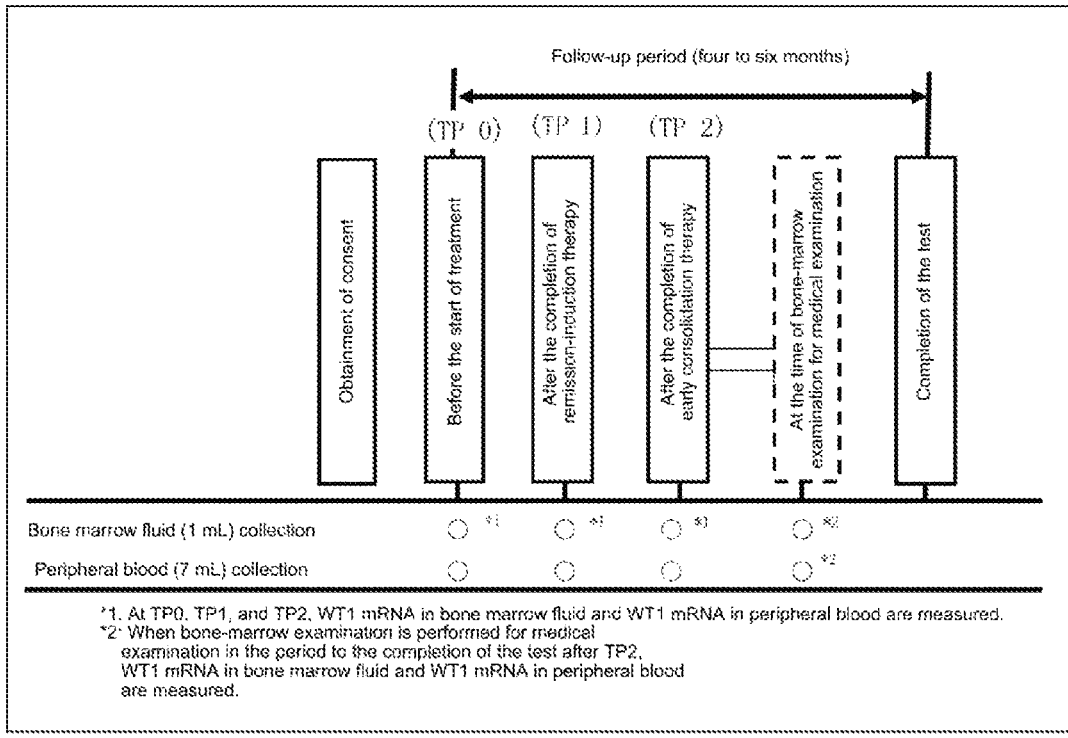
FIG. 5 shows a WT1 mRNA test schedule.
FIG. 6 shows changes in the WT1 mRNA expression level in peripheral blood and bone marrow fluid in 48 follow-up patients. In each graph, the vertical axis shows the common logarithm value of the WT1 mRNA expression level (copies/μg RNA), and the horizontal axis shows a follow-up period (months) from the start of treatment (the same applies to FIG. 7).
Figure 7A:
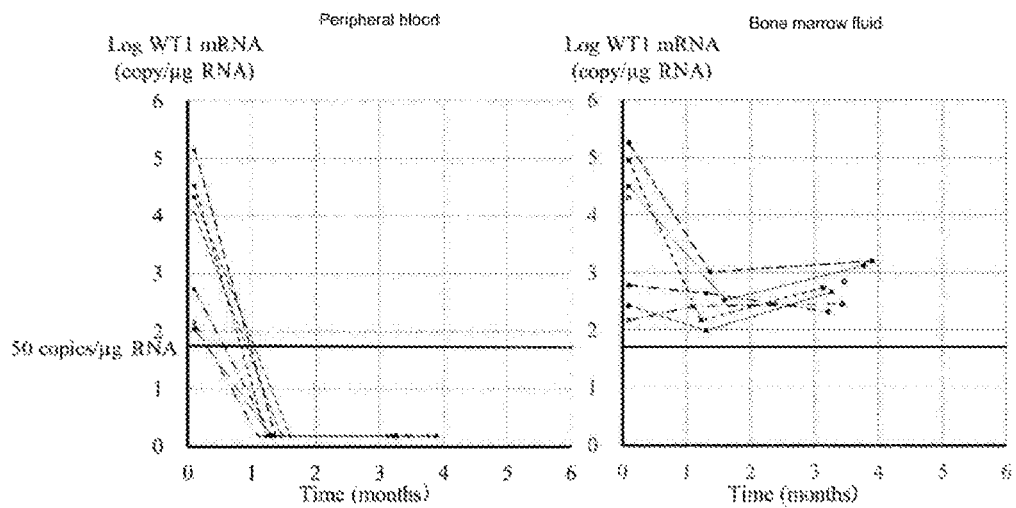
FIG. 7A shows changes in the WT1 mRNA expression level in peripheral blood and bone marrow fluid in group A (7 patients) (Table 8).
Figure 7B:
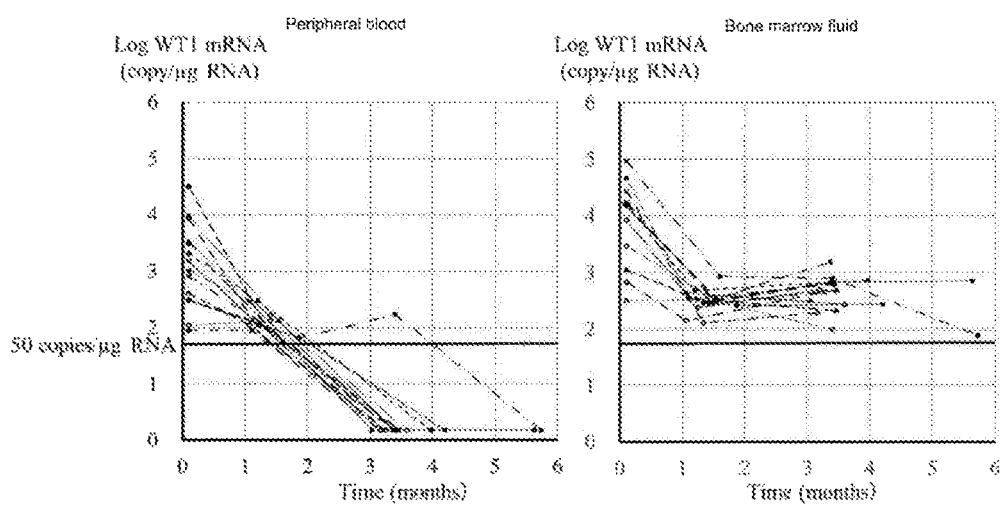
FIG. 7B shows changes in the WT1 mRNA expression level in peripheral blood and bone marrow fluid in group B (14 patients) (Table 8).
Figure 7C:
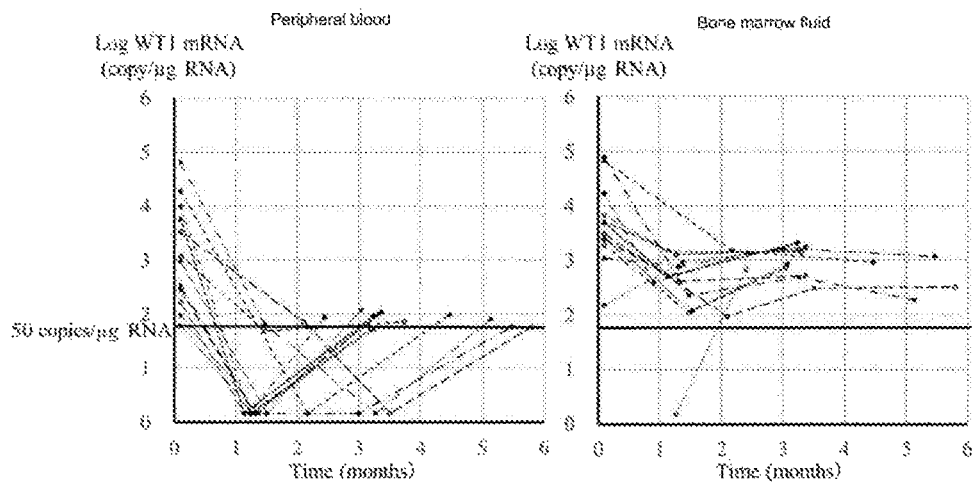
FIG. 7C shows changes in the WT1 mRNA expression level in peripheral blood and bone marrow fluid in group C (13 patients) (Table 8).
Figure 7D:
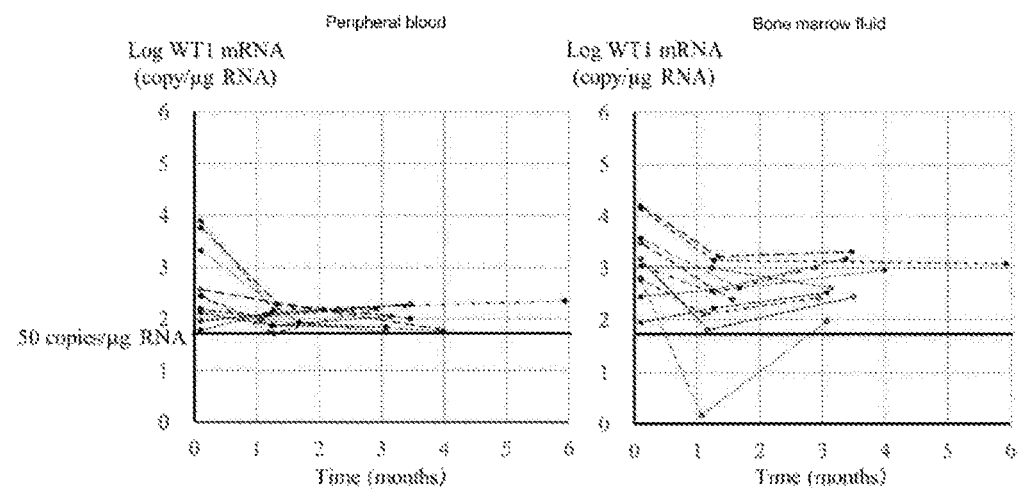
FIG. 7D shows changes in the WT1 mRNA expression level in peripheral blood and bone marrow fluid in group D (11 patients) (Table 8).
Figure 7E:
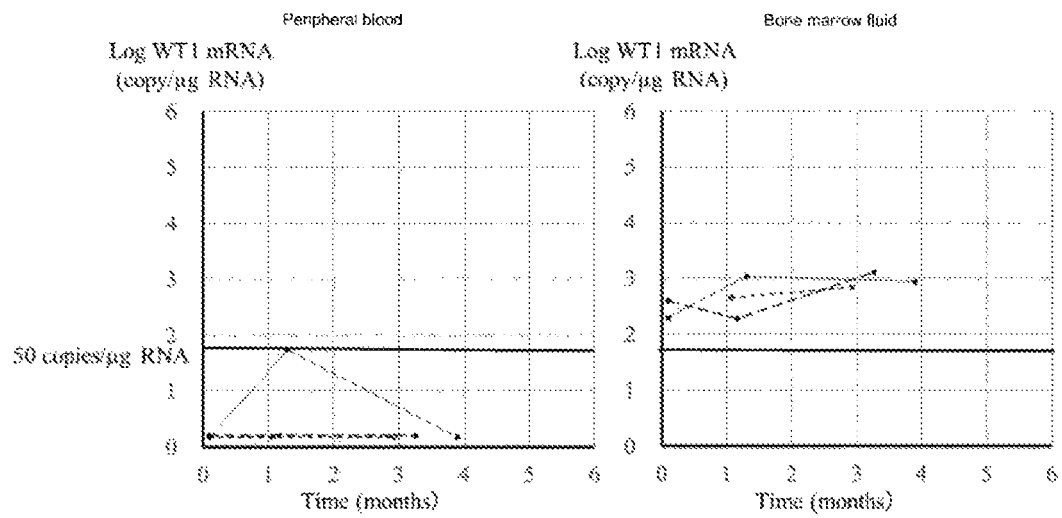
FIG. 7E shows changes in the WT1 mRNA expression level in peripheral blood and bone marrow fluid in group E (3 patients) (Table 8).

FIG. 6 shows changes in the WT1 mRNA expression level in peripheral blood and bone marrow fluid of all of the 48 patients during the follow-up period.

The WT1 mRNA expression level in peripheral blood and bone marrow fluid was calculated by multiplying a value obtained by dividing the measured value of WT1 mRNA (WT1 mRNA level) by the measured value of GAPDH mRNA (GAPDH mRNA level) (number of copies of WT1 mRNA per copy of GAPDH mRNA) by the average number of copies of GAPDH mRNA per µg RNA of healthy adults (GAPDH mRNA level=measured value of GAPDH mRNA), as shown in the following equation. The measurement of WT1 mRNA was outsourced to BML Inc.

WT1 mRNA expression level=(measured value of WT1 mRNA/measured value of GAPDH mRNA)×$2.7×10^7$ (copies/µg RNA)

$2.7×10^7$ copies/μg RNA: the average GAPDH mRNA level per μg RNA of healthy adults According to the clinical performance tests for adult ALL performed to date, the WT1 mRNA expression level in remission was less than 50 copies/μg RNA (cutoff value: 50 copies/μg RNA) in both peripheral blood and bone marrow fluid. However, in the case of patients with child ALL, the WT1 mRNA expression level is, despite the remission phase, often not less than 50 copies/μg RNA in both peripheral blood and bone marrow fluid (in particular, the WT1 mRNA expression level in bone marrow fluid) as shown in FIG. 2; therefore, it is necessary to set a new cutoff value at least larger than 50 copies/μg RNA that is different from that of adult patients with ALL.

The 48 patients were then classified into five groups, A, B, C, D, and E, based on the variation pattern of the WT1 mRNA expression level in peripheral blood, as shown in Table 8.

TABLE 8

Number of Patients in Each Variation Pattern of WT1 mRNA Expression Level during Follow-up Period

| Group | Variation pattern of WT1 mRNA expression level | Number of patients (%) |
|---|---|---|
| A | Patient in whom the WT1 mRNA expression level being 50 copies/μg RNA or more before the start of the treatment was less than 50 copies/μg RNA after the completion of the remission-induction therapy and remained less than 50 copies/μg RNA until the completion of the follow-up | 7 patients (14.6%) |
| B | Patient in whom the WT1 mRNA expression level being 50 copies/μg RNA or more before the start of the treatment decreased, but was not less than 50 copies/μg RNA after the completion of the remission-induction therapy, and became less than 50 copies/μg RNA by the completion of the follow-up | 14 patients (29.2%) |
| C | Patient in whom the WT1 mRNA expression level being 50 copies/μg RNA or more before the start of the treatment decreased to less than 50 copies/μg RNA once and then increased, and was 50 copies/μg RNA or more at the completion of the follow-up | 13 patients (27.1%) |
| D | Patient in whom the WT1 mRNA expression level being 50 copies/μg RNA or more before the start of the treatment remained 50 copies/μg RNA or more until the completion of the follow-up | 11 patients (22.9%) |
| E | Patient in whom the WT1 mRNA expression level before the treatment was less than 50 copies/μg RNA | 3 patients (6.2%) |
| | Total | 48 patients (100%) |

FIGS. 7A, 7B, 7C, 7D, and 7E show changes in the WT1 mRNA expression level in peripheral blood and the WT1 mRNA expression level in bone marrow fluid in the above five groups, A, B, C, D, and E.

In three groups, A, B, and C, of the five groups, the WT1 mRNA expression level in peripheral blood being 50 copies/μg RNA or more before the start of the treatment decreased to less than 50 copies/μg RNA at any time point in the follow-up. Since the total number of patients of these three groups was 34, the above result shows that in 70.9% of the total (34/48), the WT1 mRNA expression level in peripheral blood being 50 copies/μg RNA or more before the start of the treatment decreased to less than 50 copies/μg RNA with remission.

(3-2) WT1 mRNA Expression Level in Hematological Stages (Untreated Phase and Remission Phase)

Figure 8:
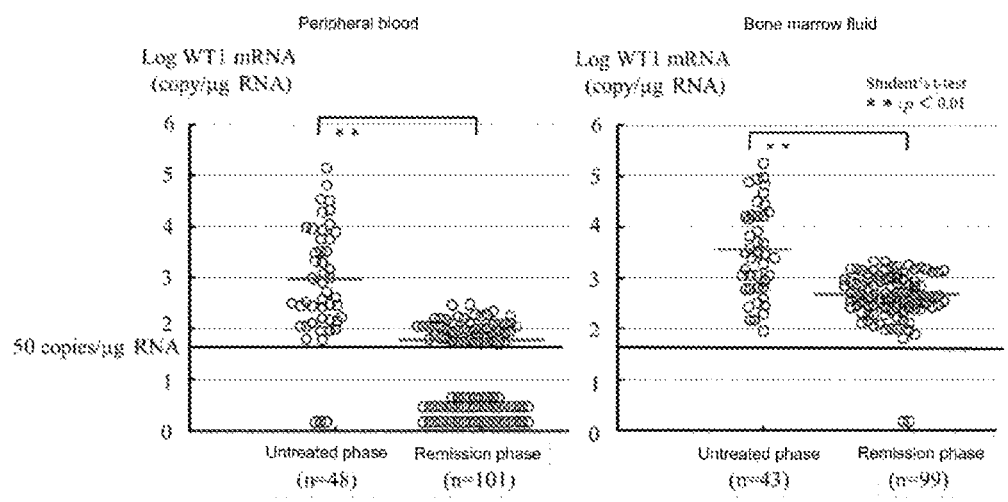
FIG. 8 shows the WT1 mRNA expression level in peripheral blood and bone marrow fluid at hematological stages. The vertical axis shows the common logarithm value of the WT1 mRNA expression level (copies/μg RNA).

Peripheral blood specimens (149 specimens) and bone marrow fluid specimens (142 specimens) of the 49 patients with child ALL, which are specimens to be analyzed, were individually divided into two groups, the untreated phase and the remission phase, and the WT1 mRNA expression levels were compared. FIG. 8 and Table 9 show the results.

TABLE 9

WT1 mRNA Expression Level in Peripheral Blood and Bone Marrow Fluid in Hematological Stages

| Hematological stage | Peripheral blood | | Bone marrow fluid | |
|---|---|---|---|---|
| | Untreated phase | Remission phase | Untreated phase | Remission phase |
| Number of specimens | 48 | 101 | 43 | 99 |
| Minimum value (copies/μg RNA) | Less than 50 | Less than 50 | 90 | Less than 50 |
| Maximum value (copies/μg RNA) | 140,000 | 300 | 180,000 | 2,100 |
| Average value (copies/μg RNA) | 910 | 70 | 3,240 | 460 |

As shown in FIG. 8 and Table 9, in the patients with child ALL, the WT1 mRNA expression level in the remission phase exhibited a significantly lower value than that in the untreated phase, in both peripheral blood and bone marrow fluid (Student's t-test, p<0.01). However, since the distributions of the WT1 mRNA expression level in both groups overlap with each other, receiver operation character (ROC) analysis was performed for both groups to examine cutoff values of the WT1 mRNA expression level, which provide an indication of remission.

Figure 9:
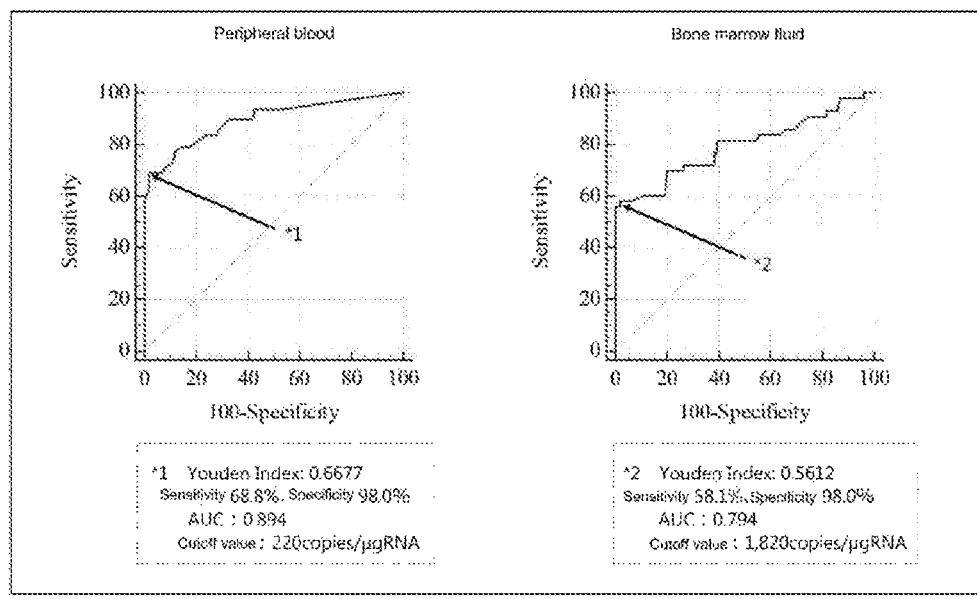
FIG. 9 shows ROC analysis results of the WT1 mRNA expression level in peripheral blood and bone marrow fluid in the remission phase and the untreated phase. The vertical axis shows sensitivity, and the horizontal axis shows specificity.

ROC curves were generated according to an ordinary method. Values with the highest specificity and sensitivity were determined to be cutoff values. FIG. 9 shows the results of the ROC analysis. As shown in FIG. 9, the following values were determined to be cutoff values for determining remission as a result of the ROC analysis: 220 copies/μg RNA in peripheral blood and 1,820 copies/μg RNA in bone marrow fluid. When the WT1 mRNA expression level being 220 copies/μg RNA was regarded as a cutoff value in peripheral blood, the sensitivity was 68.8% (33/48), and the specificity was 98.0% (99/101). Specifically, 98.0% of the peripheral blood specimens in the remission phase exhibited less than 220 copies/μg RNA. Similarly, when the WT1 mRNA expression level being 1,820 copies/µg RNA was regarded as a cutoff value in bone marrow fluid, the sensitivity was 58.1% (25/43), and the specificity was 98.0% (97/99). Specifically, 98.0% of the bone marrow fluid specimens in the remission phase exhibited less than 1,820 copies/µg RNA.

The clinical performance tests for adult ALL performed to date show that in adults, the WT1 mRNA expression level in remission was less than 50 copies/µg RNA; however, the above experiment results show that in children, even when the WT1 mRNA expression level is not less than 50 copies/µg RNA, the stage can be determined to be remission.

The results indicate that the WT1 mRNA expression level with which patients with child ALL can be determined to be in remission is less than 220 copies/µg RNA in peripheral blood and less than 1,820 copies/µg RNA in bone marrow fluid, and that when a patient with child ALL satisfies at least one of these, it can be determined that the patient has entered the remission phase.

DESCRIPTION OF THE REFERENCE NUMERALS

1 Determination assist device
2 Measurement device
3 Computer system
3a Computer body
3b Input unit
3c Display unit
30 CPU
31 ROM
32 RAM
33 Auxiliary storage unit
34 Input-output interface
35 Media interface
36 Communication interface
37 Image-output interface
38 Bus
40 Recording medium
301 Reception unit
302 Storage unit
303 Calculation unit
304 Determination unit
305 Output unit

The invention claimed is:

1. A method for making a determination with respect to a hematological stage of childhood acute lymphoblastic leukemia (child ALL), the method comprising the steps of:
(1) obtaining an mRNA level of Wilms' tumor-1 gene (WT1) in a biological sample of a test subject, wherein said test subject is a patient with child ALL or suspected child ALL;
(2) obtaining an mRNA level of glyceraldehyde-3-phosphate dehydrogenase (GAPDH) in the biological sample;
(3) calculating an index value by normalizing the mRNA level of the WT1 obtained in step (1) to the mRNA level of GAPDH obtained in step (2);
(4) comparing the index value calculated in step (3) with a predetermined cutoff value, wherein the predetermined cutoff value distinguishes between an average of index values calculated by normalizing mRNA levels of WT1 mRNA to mRNA levels of GAPDH mRNA of children affected by child ALL and an average of index values calculated by normalizing mRNA levels of WT1 mRNA to mRNA levels of GAPDH of children in remission phase of child ALL and/or children who are not affected by child ALL; and
(5) making a determination that
   (a) said test subject is in the remission phase when said test subject is a patient with child ALL, and when the index value obtained in step (3) is smaller than said predetermined cutoff value;
   (b) said test subject is in the non-remission phase when said test subject is a patient with child ALL, and when the index value obtained in step (3) is equal to or larger than said predetermined cutoff value;
   (c) said test subject is not affected by child ALL when said test subject is a patient with suspected child ALL, and when the index value obtained in step (3) is smaller than said predetermined cutoff value; or
   (d) said test subject is affected by child ALL when said test subject is a patient with suspected child ALL, and when the index value obtained in step (3) is equal to or larger than said predetermined cutoff value; and
(6) performing one or more of the following steps:
   (a) displaying the determination result on a display;
   (b) printing the determination result;
   (c) recording the determination result on a recording medium;
   (d) storing the determination result on a storage unit or on an auxiliary storage unit; and
   (e) providing the determination result to an output unit;
wherein the mRNA level in step (1) or (2) is measured using RT-PCR, in situ RT-PCR, or next-generation sequencing.

2. A method for making a determination with respect to a hematological stage of childhood acute lymphoblastic leukemia (child ALL), the method comprising the steps of:
(1) obtaining an mRNA level of Wilms' tumor-1 gene (WT1) in a biological sample of a test subject, wherein said test subject is a patient with child ALL or suspected child ALL;
(2) obtaining an mRNA level of glyceraldehyde-3-phosphate dehydrogenase (GAPDH) in the biological sample;
(3) calculating an index value by normalizing the mRNA level of the WT1 obtained in step (1) to the mRNA level of GAPDH obtained in step (2);
(4) comparing the index value calculated in step (3) with a predetermined cutoff value; and
(5) making a determination that
   (a) said test subject is in the remission phase when said test subject is a patient with child ALL, and when the index value obtained in step (3) is smaller than said predetermined cutoff value;
   (b) said test subject is in the non-remission phase when said test subject is a patient with child ALL, and when the index value obtained in step (3) is equal to or larger than said predetermined cutoff value;
   (c) said test subject is not affected by child ALL when said test subject is a patient with suspected child ALL, and when the index value obtained in step (3) is smaller than said predetermined cutoff value; or
   (d) said test subject is affected by child ALL when said test subject is a patient with suspected child ALL, and when the index value obtained in step (3) is equal to or larger than said predetermined cutoff value; and
(6) performing one or more of the following steps:
   (a) displaying the determination result on a display;
   (b) printing the determination result;
   (c) recording the determination result on a recording medium;
   (d) storing the determination result on a storage unit or on an auxiliary storage unit; and
   (e) providing the determination result to an output unit;
wherein the mRNA level in step (1) or (2) is measured using RT-PCR, in situ RT-PCR, or next-generation sequencing;
wherein the normalization is performed by multiplying the ratio of the WT1 mRNA level to the GAPDH mRNA level (WT1 mRNA level/GAPDH mRNA level) by $2.7 \times 10^7$ copies/ug RNA, which is an average value of GAPDH mRNA levels contained in 1 μg RNA of healthy adults.

3. A method for making a determination with respect to a hematological stage of childhood acute lymphoblastic leukemia (child ALL), the method comprising the steps of:
(1) obtaining an mRNA level of Wilms' tumor-1 gene (WT1) in a biological sample of a test subject, wherein said test subject is a patient with child ALL or suspected child ALL;
(2) obtaining an mRNA level of glyceraldehyde-3-phosphate dehydrogenase (GAPDH) in the biological sample;
(3) calculating an index value by normalizing the mRNA level of the WT1 obtained in step (1) to the mRNA level of GAPDH obtained in step (2);
(4) comparing the index value calculated in step (3) with a predetermined cutoff value; and
(5) making a determination that
   (a) said test subject is in the remission phase when said test subject is a patient with child ALL, and when the index value obtained in step (3) is smaller than said predetermined cutoff value;
   (b) said test subject is in the non-remission phase when said test subject is a patient with child ALL, and when the index value obtained in step (3) is equal to or larger than said predetermined cutoff value;
   (c) said test subject is not affected by child ALL when said test subject is a patient with suspected child ALL, and when the index value obtained in step (3) is smaller than said predetermined cutoff value; or
   (d) said test subject is affected by child ALL when said test subject is a patient with suspected child ALL, and when the index value obtained in step (3) is equal to or larger than said predetermined cutoff value; and (6) performing one or more of the following steps:
(a) displaying the determination result on a display;
(b) printing the determination result;
(c) recording the determination result on a recording medium;
(d) storing the determination result on a storage unit or on an auxiliary storage unit; and
(e) providing the determination result to an output unit;

wherein the mRNA level in step (1) or (2) is measured using RT-PCR, in situ RT-PCR, or next-generation sequencing;

wherein the determination is to distinguish between the remission phase and the non-remission phase of child ALL; and the cutoff value is determined by statistical analysis of both groups of patients with child ALL in a non-remission phase (a group in a non-remission phase) and patients with child ALL in a remission phase (a group in a remission-phase), and wherein the biological sample is selected from the group consisting of peripheral blood and bone marrow fluid; and wherein the cutoff value is 220 copies/ug RNA if the biological sample is peripheral blood, and 1,820 copies/ug RNA if the biological sample is bone marrow fluid.

4. The method according to claim 1, wherein the mRNA level in step (1) or (2) is measured using RT-PCR.

5. The method according to claim 4, wherein in said RT-PCR, reverse transcription and extension reactions of the WT1 mRNA and the GAPDH mRNA occur simultaneously in the same container.

6. The method according to claim 4, wherein said RT-PCR employs, for the measurement of the WT1 mRNA level, (a) a primer set comprising a forward PCR primer that contains the base sequence represented by SEQ ID NO: 2 and a reverse PCR primer that contains the base sequence represented by SEQ ID NO: 3; or (b) a primer set comprising a forward PCR primer that contains the base sequence represented by SEQ ID NO: 5 and a reverse PCR primer that contains the base sequence represented by SEQ ID NO: 6.

7. The method according to claim 4, wherein said RT-PCR employs, for the measurement of the WT1 mRNA level, (a') a primer set comprising a forward PCR primer that contains the base sequence represented by SEQ ID NO: 2 and a reverse PCR primer that contains the base sequence represented by SEQ ID NO: 3, and a labeled probe that contains the base sequence represented by SEQ ID NO: 4; or (b') a primer set comprising a forward PCR primer that contains the base sequence represented by SEQ ID NO: 5 and a reverse PCR primer that contains the base sequence represented by SEQ ID NO: 6, and a labeled probe that contains the base sequence represented by SEQ ID NO: 7.

8. The method according to claim 4, wherein said RT-PCR employs, for the measurement of the GAPDH mRNA level, (c) a primer set comprising a forward PCR primer that contains the base sequence represented by SEQ ID NO: 9 and a reverse PCR primer that contains the base sequence represented by SEQ ID NO: 10 or 12.

9. The method according to claim 4, wherein said RT-PCR employs, for the measurement of the GAPDH mRNA level, (c') a primer set comprising a forward PCR primer that contains the base sequence represented by SEQ ID NO: 9 and a reverse PCR primer that contains the base sequence represented by SEQ ID NO: 10 or 12, and a labeled probe that contains the base sequence represented by SEQ ID NO: 11.

10. A method for monitoring a hematological stage of child ALL over time, comprising performing the method of claim 1 on biological samples obtained from a test subject at different times.

11. The method according to claim 10, wherein the method monitors transition from a non-remission phase to a remission phase, and/or a transition from a remission phase to a non-remission phase.

12. The method according to claim 1, wherein step (3) is performed by a computer, wherein a computer program causes the computer to execute said step.

13. The method according to claim 1, wherein steps (3), (4) and (5) are performed by a computer, wherein a computer program causes the computer to execute said steps.

14. The method according to claim 12, wherein the computer program is recorded in a memory of a computer system comprising the computer that includes a processor and the memory.

15. The method according to claim 13, wherein the computer program is recorded in a memory of a computer system comprising the computer that includes a processor and the memory.

* * * * *

SEQUENCE LISTING

```
<160> NUMBER OF SEQ ID NOS: 12

<210> SEQ ID NO 1
<211> LENGTH: 3037
<212> TYPE: DNA
<213> ORGANISM: Homo sapiens

<400> SEQUENCE: 1
agctggggta aggagttcaa ggcagcgccc acacccgggg gctctccgca acccgaccgc    60
ctgtccgctc ccccacttcc cgccctccct cccacctact cattcaccca cccacccacc   120
cagagccggg acggcagccc aggcgccggg gccccgccgt ctcctcgccg cgatcctgga   180
cttcctcttg ctgcaggacc cggcttccac gtgtgtcccg gagccggcgt ctcagcacac   240
gctccgctcc gggcctgggt gcctacagca gccagagcag cagggagtcc gggacccggg   300
cggcatctgg gccaagttag gcgccgccga ggccagcgct gaacgtctcc agggccggag   360
gagccgcggg gcgtccgggt ctgagccgca gcaaatgggc tccgacgtgc gggacctgaa   420
cgcgctgctg cccgccgtcc cctccctggg tggcggcggc ggctgtgccc tgcctgtgag   480
cggcgcggcg cagtgggcgc cggtgctgga ctttgcgccc ccgggcgctt cggcttacgg   540
gtcgttgggc ggccccgcgc cgccaccggc tccgccgcca ccccgccgc cgccgcctca   600 ctccttcatc aaacaggagc cgagctgggg cggcgcggag ccgcacgagg agcagtgcct   660
gagcgccttc actgtccact tttccggcca gttcactggc acagccggag cctgtcgcta   720
cgggcccttc ggtcctcctc cgcccagcca ggcgtcatcc ggccaggcca ggatgtttcc   780
taacgcgccc tacctgccca gctgcctcga gagccagccc gctattcgca atcagggtta   840
cagcacggtc accttcgacg ggacgcccag ctacggtcac acgccctcgc accatgcggc   900
gcagttcccc aaccactcat tcaagcatga ggatcccatg ggccagcagg gctcgctggg   960
tgagcagcag tactcggtgc cgcccccggt ctatggctgc cacaccccca ccgacagctg  1020
caccggcagc caggctttgc tgctgaggac gcctacagc agtgacaatt tataccaaat  1080
gacatcccag cttgaatgca tgacctggaa tcagatgaac ttaggagcca ccttaaaggg  1140
```

-continued

```
agttgctgct gggagctcca gctcagtgaa atggacagaa gggcagagca accacagcac    1200
agggtacgag agcgataacc acacaacgcc catcctctgc ggagcccaat acagaataca    1260
cacgcacggt gtcttcagag gcattcagga tgtgcgacgt gtgcctggag tagcccccgac   1320
tcttgtacgg tcggcatctg agaccagtga gaaacgcccc ttcatgtgtg cttacccagg    1380
ctgcaataag agatatttta agctgtccca cttacagatg cacagcagga agcacactgg    1440
tgagaaacca taccagtgtg acttcaagga ctgtgaacga aggttttctc gttcagacca    1500
gctcaaaaga caccaaagga gacatacagg tgtgaaacca ttccagtgta aaacttgtca    1560
gcgaaagttc tcccggtccg accacctgaa gacccacacc aggactcata caggtaaaac    1620
aagtgaaaag cccttcagct gtcggtggcc aagttgtcag aaaaagtttg cccggtcaga    1680
tgaattagtc cgccatcaca acatgcatca gagaaacatg accaaactcc agctggcgct    1740
ttgagggggtc tccctcgggg accgttcagt gtcccaggca gcacagtgtg tgaactgctt   1800
tcaagtctga ctctccactc ctcctcacta aaaaggaaac ttcagttgat cttcttcatc    1860
caacttccaa gacaagatac cggtgcttct ggaaactacc aggtgtgcct ggaagagttg    1920
gtctctgccc tgcctacttt tagttgactc acaggccctg gagaagcagc taacaatgtc    1980
tggttagtta aaagcccatt gccatttggt gtggattttc tactgtaaga gagccatag    2040
ctgatcatgt cccctgacc cttcccttct ttttttatgc tcgttttcgc tggggatgga    2100
attattgtac cattttctat catggaatat ttataggcca gggcatgtgt atgtgtctgc    2160
taatgtaaac tttgtcatgg tttccattta ctaacagcaa cagcaagaaa taatcagag    2220
agcaaggcat cgggggtgaa tcttgtctaa cattcccgag gtcagccagg ctgctaacct    2280
ggaaagcagg atgtagttct gccaggcaac ttttaaagct catgcatttc aagcagctga    2340
agaaaaaatc agaactaacc agtacctctg tatagaaatc taaagaatt ttaccattca     2400
gttaattcaa tgtgaacact ggcacactgc tcttaagaaa ctatgaagat ctgagatttt    2460
tttgtgtatg ttttttgactc ttttgagtgg taatcatatg tgtctttata gatgtacata   2520
cctccttgca caaatggagg ggaattcatt ttcatcactg ggagtgtcct tagtgtataa    2580
aaaccatgct ggtatatggc ttcaagttgt aaaaatgaaa gtgactttaa agaaaatag    2640
gggatggtcc aggatctcca ctgataagac tgtttttaag taacttaagg accttttgggt   2700
ctacaagtat atgtgaaaaa aatgagactt actgggtgag gaaatccatt gtttaaagat    2760
ggtcgtgtgt gtgtgtgtgt gtgtgtgtgt gtgtgtgttg tgttgtgttt tgttttttaa    2820
gggagggaat ttattattta ccgttgcttg aaattactgt gtaaatatat gtctgataat    2880
gatttgctct ttgacaacta aaattaggac tgtataagta ctagatgcat cactgggtgt    2940
tgatcttaca agatattgat gataacactt aaaattgtaa cctgcatttt tcactttgct    3000
ctcaattaaa gtctattcaa aaggaaaaaa aaaaaaa                             3037
```

```
<210> SEQ ID NO 2
<211> LENGTH: 22
<212> TYPE: DNA
<213> ORGANISM: Artificial Sequence
<220> FEATURE:
<223> OTHER INFORMATION: Synthetic Sequence, (A1) Forward Primer

<400> SEQUENCE: 2
cgctattcgc aatcagggtt ac                                              22

<210> SEQ ID NO 3
<211> LENGTH: 22
```

```
<212> TYPE: DNA
<213> ORGANISM: Artificial Sequence
<220> FEATURE:
<223> OTHER INFORMATION: Synthetic Sequence, (A2) Reverse Primer

<400> SEQUENCE: 3
ggatcctcat gcttgaatga gt                                               22

<210> SEQ ID NO 4
<211> LENGTH: 22
<212> TYPE: DNA
<213> ORGANISM: Artificial Sequence
<220> FEATURE:
<223> OTHER INFORMATION: Synthetic Sequence, (A3) Probe

<400> SEQUENCE: 4
agcacggtca ccttcgacgg ga                                               22

<210> SEQ ID NO 5
<211> LENGTH: 21
<212> TYPE: DNA
<213> ORGANISM: Artificial Sequence
<220> FEATURE:
<223> OTHER INFORMATION: Synthetic Sequence, (B1) Forward Primer

<400> SEQUENCE: 5
gataaccaca caacgcccat c                                                21

<210> SEQ ID NO 6
<211> LENGTH: 21
<212> TYPE: DNA
<213> ORGANISM: Artificial Sequence
<220> FEATURE:
<223> OTHER INFORMATION: Synthetic Sequence, (B2) Reverse Primer

<400> SEQUENCE: 6
cacacgtcgc acatcctgaa t                                                21

<210> SEQ ID NO 7
<211> LENGTH: 26
<212> TYPE: DNA
<213> ORGANISM: Artificial Sequence
<220> FEATURE:
<223> OTHER INFORMATION: Synthetic Sequence, (B3) Probe

<400> SEQUENCE: 7
aatacacacg cacggtgtct tcagag                                           26

<210> SEQ ID NO 8
<211> LENGTH: 1310
<212> TYPE: DNA
<213> ORGANISM: Homo sapiens

<400> SEQUENCE: 8
aaattgagcc cgcagcctcc cgcttcgctc tctgctcctc ctgttcgaca gtcagccgca      60
tcttcttttg cgtcgccagc cgagccacat cgctcagaca ccatggggaa ggtgaaggtc     120
ggagtcaacg gatttggtcg tattgggcgc ctggtcacca gggctgcttt taactctggt     180
aaagtggata ttgttgccat caatgacccc ttcattgacc tcaactacat ggtttacatg     240
ttccaatatg attccaccca tggcaaattc catggcaccg tcaaggctga aacgggaag      300 cttgtcatca atggaaatcc catcaccatc ttccaggagc gagatccctc caaaatcaag     360
tggggcgatg ctggcgctga gtacgtcgtg gagtccactg cgtcttcac caccatggag     420
```

```
aaggctgggg ctcatttgca ggggggagcc aaaagggtca tcatctctgc cccctctgct    480
gatgccccca tgttcgtcat gggtgtgaac catgagaagt atgacaacag cctcaagatc    540
atcagcaatg cctcctgcac caccaactgc ttagcacccc tggccaaggt catccatgac    600
aactttggta tcgtggaagg actcatgacc acagtccatg ccatcactgc cacccagaag    660
actgtggatg gcccctccgg gaaactgtgg cgtgatggcc gcgggctct  ccagaacatc    720 atccctgcct ctactggcgc tgccaaggct gtgggcaagg tcatccctga gctgaacggg    780
aagctcactg gcatggcctt ccgtgtcccc actgccaacg tgtcagtggt ggacctgacc    840
tgccgtctag aaaaacctgc caaatatgat gacatcaaga aggtggtgaa gcaggcgtcg    900
gagggccccc tcaagggcat cctgggctac actgagcacc aggtggtctc ctctgacttc    960
aacagcgaca cccactcctc cacctttgac gctggggctg gcattgccct caacgaccac   1020
tttgtcaagc tcatttcctg gtatgacaac gaatttggct acagcaacag ggtggtggac   1080
ctcatggccc acatggcctc caaggagtaa gaccccctgga ccaccagccc cagcaagagc   1140
acaagaggaa gagagagacc ctcactgctg gggagtccct gccacactca gtcccccacc   1200
acactgaatc tcccctcctc acagttgcca tgtagacccc ttgaagaggg gaggggccta   1260
gggagccgca ccttgtcatg taccatcaat aaagtaccct gtgctcaacc               1310

<210> SEQ ID NO 9
<211> LENGTH: 16
<212> TYPE: DNA
<213> ORGANISM: Artificial Sequence
<220> FEATURE:
<223> OTHER INFORMATION: Synthetic Sequence, (a1) Forward Primer

<400> SEQUENCE: 9
cagccgagcc acatcg                                                     16

<210> SEQ ID NO 10
<211> LENGTH: 22
<212> TYPE: DNA
<213> ORGANISM: Artificial Sequence
<220> FEATURE:
<223> OTHER INFORMATION: Synthetic Sequence, (a2) Reverse Primer

<400> SEQUENCE: 10
gtcaatgaag gggtcattga tg                                              22

<210> SEQ ID NO 11
<211> LENGTH: 21
<212> TYPE: DNA
<213> ORGANISM: Artificial Sequence
<220> FEATURE:
<223> OTHER INFORMATION: Synthetic Sequence, (a3) Probe

<400> SEQUENCE: 11
ttggtcgtat tgggcgcctg g                                               21

<210> SEQ ID NO 12
<211> LENGTH: 25
<212> TYPE: DNA
<213> ORGANISM: Artificial Sequence
<220> FEATURE:
<223> OTHER INFORMATION: Synthetic Sequence, (b2) Reverse Primer

<400> SEQUENCE: 12
tgatggcaac aatatccact ttacc                                           25
```